US006331178B1

United States Patent
Loeb et al.

(10) Patent No.: US 6,331,178 B1
(45) Date of Patent: Dec. 18, 2001

(54) USER ACTUATED LASER ENERGY DEVICE AND PROCEDURE FOR FORMING A CHANNEL WITHIN TISSUE

(75) Inventors: Marvin P. Loeb, Huntington Beach; Samuel M. Shaolian, Laguna Niguel, both of CA (US)

(73) Assignee: Cardiodyne, Inc., Irvine, CA (US)

( * ) Notice: Subject to any disclaimer, the term of this patent is extended or adjusted under 35 U.S.C. 154(b) by 0 days.

(21) Appl. No.: 09/456,275

(22) Filed: Dec. 7, 1999

Related U.S. Application Data

(63) Continuation of application No. 09/015,391, filed on Jan. 29, 1998, now Pat. No. 5,997,531.

(51) Int. Cl.[7] .................................................. A61B 18/18
(52) U.S. Cl. ................................................ 606/13; 606/15
(58) Field of Search ....................... 606/2, 13–16, 606/11

(56) References Cited

U.S. PATENT DOCUMENTS

| | | | | |
|---|---|---|---|---|
| 4,959,063 | * | 9/1990 | Kojima ..................................... | 606/15 |
| 5,578,029 | * | 11/1996 | Trelles et al. ........................... | 606/25 |
| 5,591,159 | * | 1/1997 | Taheri ..................................... | 606/15 |
| 5,713,894 | * | 2/1998 | Murphy-Churtorian et al. ..... | 606/15 |
| 5,738,680 | * | 4/1998 | Mueller et al. ......................... | 606/15 |
| 5,766,164 | * | 6/1998 | Mueller et al. ......................... | 606/15 |
| 6,056,742 | * | 5/2000 | Murphy-Chutorian et al. ....... | 606/11 |

* cited by examiner

*Primary Examiner*—Roy Gibson
(74) *Attorney, Agent, or Firm*—Olson & Hierl, Ltd.

(57) ABSTRACT

A surgical device is provided for forming a channel through or into tissue utilizing both mechanical energy and laser energy. The device includes a needle for forming the first part of the channel. The needle has an open bore. Mounted within the bore is an optical fiber for emitting laser energy to form the balance of the channel.

3 Claims, 22 Drawing Sheets

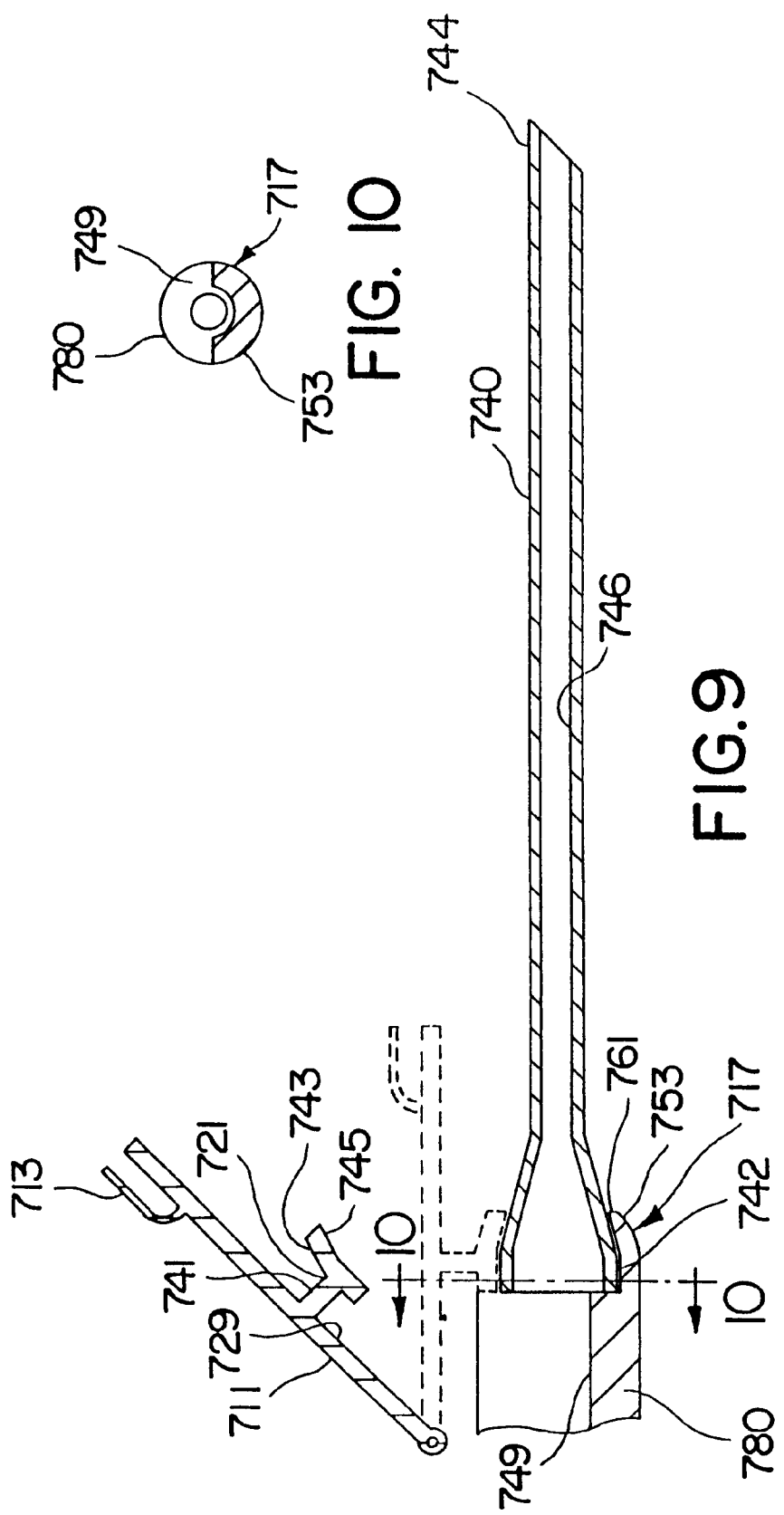

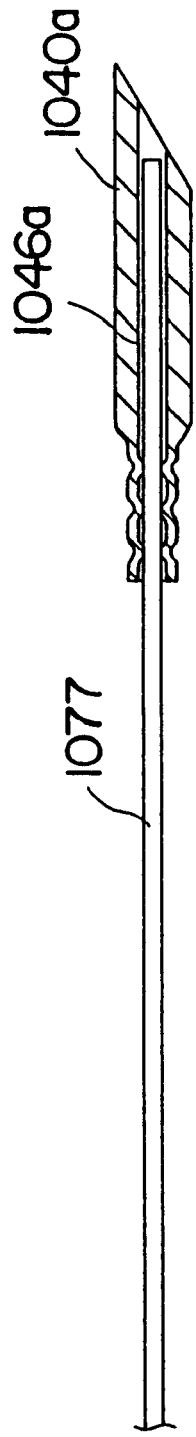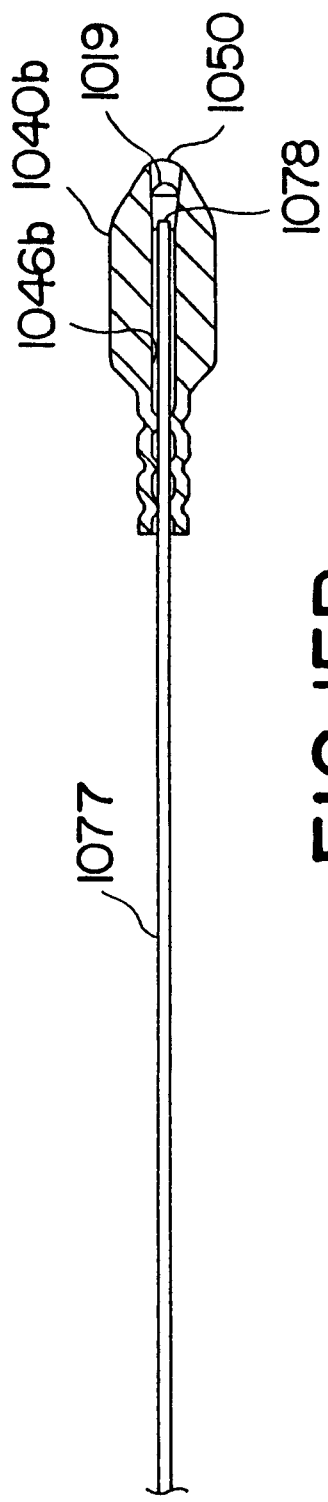

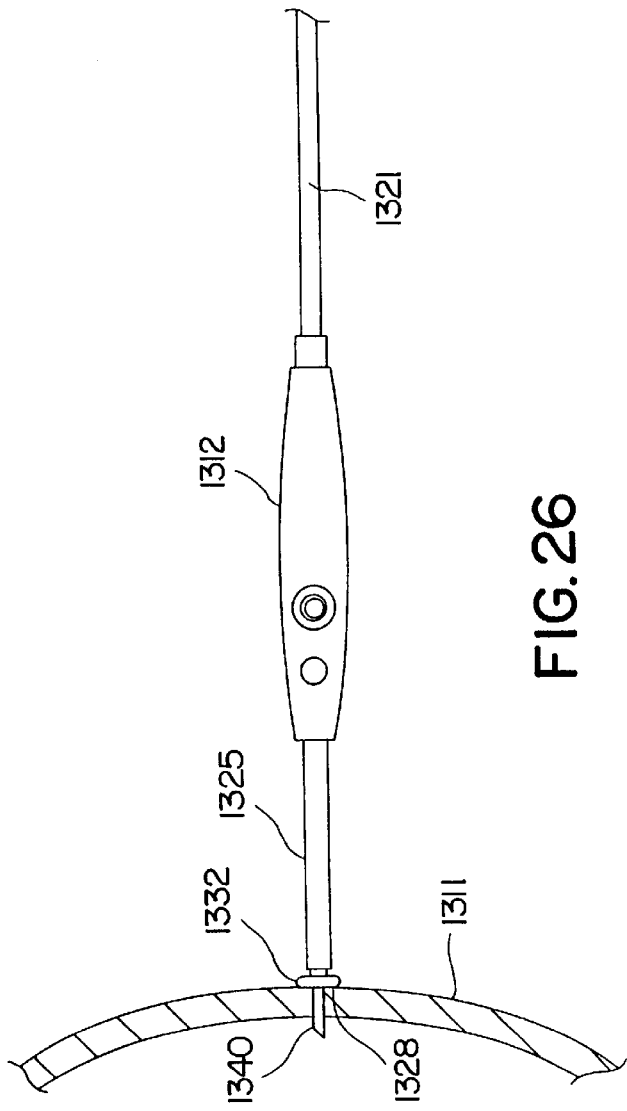
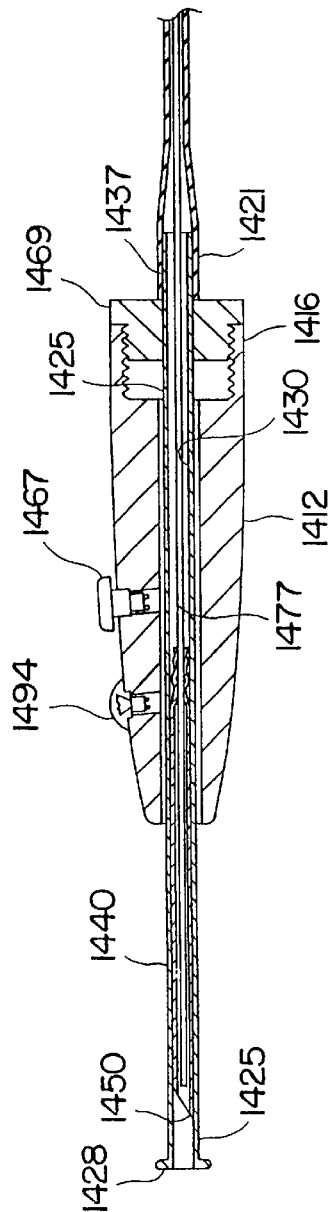

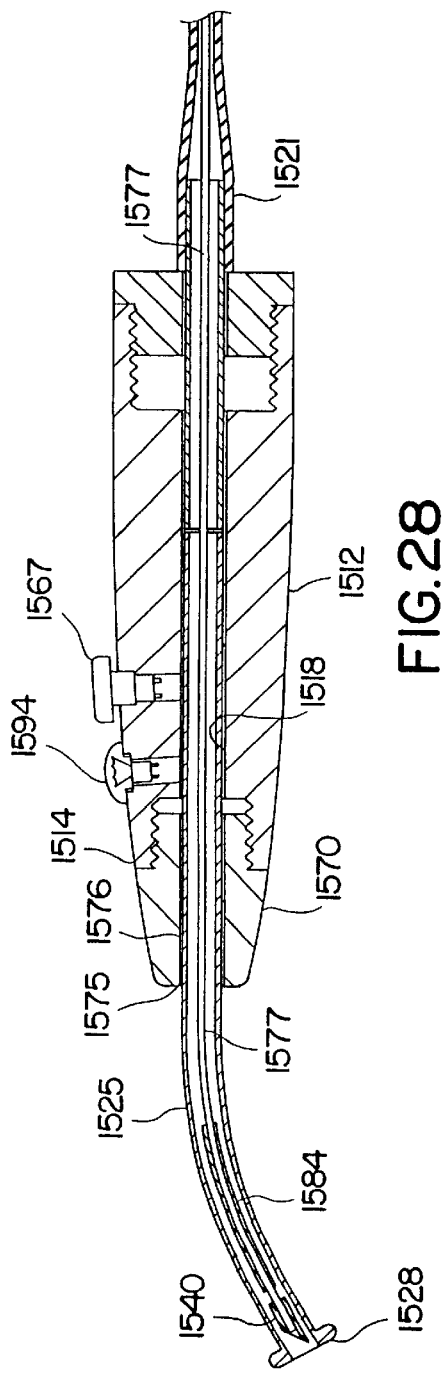
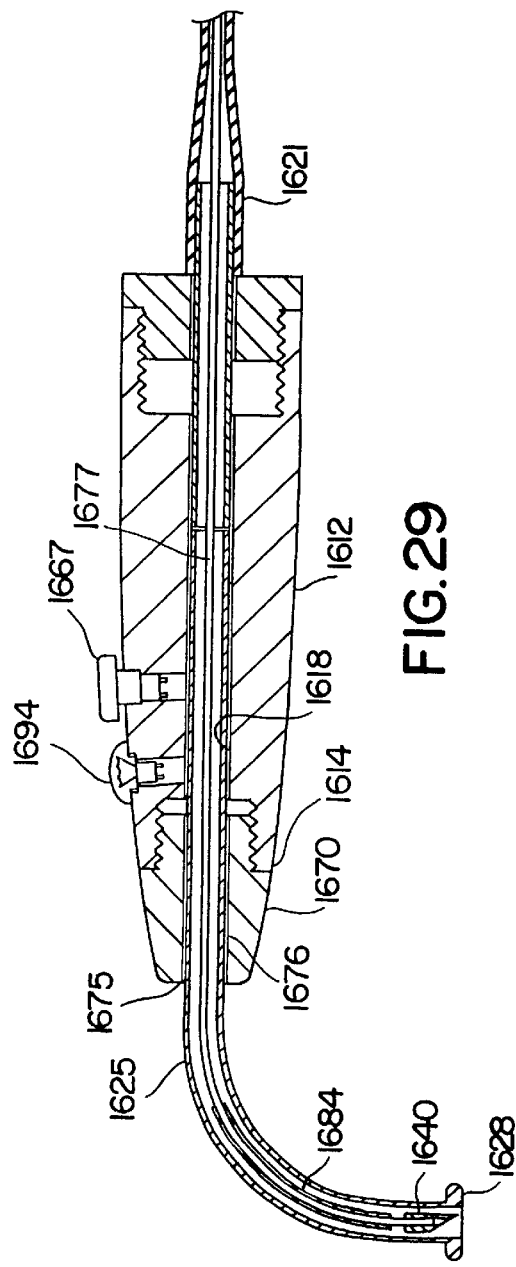

USER ACTUATED LASER ENERGY DEVICE AND PROCEDURE FOR FORMING A CHANNEL WITHIN TISSUE

This application is a continuation of application Ser. No. 09/015,391, filed Jan. 29, 1998, now U.S. Pat. No. 5,997,531.

FIELD OF THE INVENTION

The present invention relates to surgical devices and procedures for the delivery of a combination of mechanical and laser energy to form a channel within tissue, and in particular to a device and procedure which forms a channel partially by mechanical energy and partially by emitting laser energy directly onto the tissue.

BACKGROUND OF THE INVENTION

A human heart receives its blood supply from the coronary arteries which branch out and around the heart muscle. Conversely, in a reptile, little or no arterial supply of blood is provided to the heart muscle. Instead, the blood supply is mainly delivered through the inside wall of the heart chamber.

Modifying a human heart to imitate the blood delivery method of a reptile heart is currently being used as an alternative or adjunct to coronary artery bypass graft surgery and coronary balloon angioplasty. Normally, a person can only undergo coronary bypass surgery twice, since the risks will begin to outweigh the benefits after that point. Thus, in the past, a patient who has already had two coronary bypass surgeries was left with no recourse. Others have failed repeated coronary balloon angioplasties, and many persons are not suitable candidates for coronary bypass surgery or coronary balloon angioplasty. These persons likewise are left with no recourse.

Early attempts to imitate the reptilian condition in mammals, known as transmyocardial revascularization (TMR), consisted of producing tiny channels in mammalian and human hearts with needles or hot wires. This method met with limited success since, although the channels closed by clotting at the outside surface of the heart, due to exposure to air, and did allow for some internal blood delivery, the channels soon healed over entirely and failed to continue the blood supply. Early attempts were also made to graft a blood vessel from the aorta directly into the heart muscle to provide an internal source of blood. While some benefits were seen, the surgery was technically demanding and the procedure was eclipsed by the introduction of coronary artery bypass graft surgery.

To overcome these problems, Mahmood Mirhoseini and Mary M. Cayton suggest transmyocardial revascularization by using a high-powered $CO_2$ laser to make the channels. Mirhoseini M., Cayton M. M., *Revascularization of the Heart by Laser*, J Microsurg 2:253, June, 1981. The laser forms each channel by vaporizing a passageway completely through the wall of the heart. The relatively clean channel formed by the laser energy prevents the channel from healing over, and the channel either closes by clotting at the heart's outer surface, due to exposure to air, or manual pressure can be applied until bleeding from the channel ceases. However, if bleeding cannot be stopped, or if bleeding resumes at a later time, the patient may require surgery or may die.

Generally, it is desired that the channels be made primarily within the heart's inner surface (endocardium) since the endocardium has a greater need of an alternative supply of blood than the heart's outer surface (epicardium). It would be desirable not to create too large a channel through the epicardium because the channel must clot and/or heal at the heart's surface to prevent copious blood loss due to the forceful pumping action of the heart. It would be desirable to produce a channel which is widest at the point the channel exits the inner surface of the heart chamber, admitting a larger volume of blood and being less susceptible to clotting or healing.

The current laser devices used to perform transmyocardial revascularization are inefficient at creating desirably shaped channels within the endocardium. For instance, a high power (i.e., 1,000 watt) carbon dioxide laser, whose beam is focused at the heart's surface, can make a channel completely through the heart wall in one shot in approximately 50 milliseconds, during diastole, when the heart is momentarily at rest. The channel, however, is usually wider in the epicardium than in the endocardium, making clotting or healing at the heart's outer surface less secure and making closure at the heart's inner surface more likely.

The prior art also uses several mirrors to reflect carbon dioxide laser energy toward the tissue to be vaporized. Maintaining the proper alignment of these mirrors at all times, however, is difficult and inconvenient for the operator.

Further, the use of less powerful lasers whose energy can be transmitted through optical fibers, such as argon-ion have also been proposed. Lee G. et al., *Effects of Laser Irradiation Delivered by Flexible Fiberoptic System on the Left Ventricular internal Myocardium*, Am Heart J., September, 1983. However, if the laser energy is applied to make the channel completely through the heart wall, the laser must be operated for a longer period of time than if it were used only to form a channel through the endocardium. If the procedure cannot be completed during diastole, within approximately 0.6 seconds, between heartbeats when the heart's electrical activity is minimal, a life threatening arrhythmia may result, and damage to the heart muscle during its compression may occur.

The present invention provides an improved device and procedure which overcomes the above-discussed problems by combining mechanical energy with laser energy and enabling the laser energy to be emitted directly onto the tissue to be vaporized.

SUMMARY OF THE INVENTION

The present invention provides a device and procedure for utilizing mechanical energy to create a channel through the epicardium, which seals more quickly and dependably than a laser created channel, and delivering laser energy directly onto all of the endocardial tissue that must be vaporized in order to form a channel into the heart chamber.

The device embodying the present invention is especially suitable for use in medical applications for delivering laser energy to a selected tissue site at a controlled rate in a uniform manner, so the depth of coagulation surrounding the channel can be controlled as desired. In addition, the present device reduces the amount of laser energy required to form a channel, as penetration of the epicardium is achieved by mechanical means. Furthermore, the present device allows formation of uniformly or otherwise desirably shaped channels between heartbeats in a periodically moving structure such as a human heart.

A surgical device embodying the present invention includes a housing, an optical fiber secured to the housing for transmitting laser energy, and a hollow needle surrounding at least a portion of the optical fiber. An actuator rod is provided to actuate the transmission of laser energy. The actuator rod can also actuate a mechanism to extend the optical fiber or the needle, and the optical fiber contained therewithin, from the housing and into the tissue at the site where a channel is to be formed. The channel is formed by energizing, at a desired distance within the tissue, a suitable laser source and passing a laser beam from the source through the optical fiber into the tissue.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIG. 9 is a partial enlarged cross-sectional side view of the device shown in FIG. 7 with the door open and, depicted in phantom, with the door closed;

FIG. 10 is a cross-sectional end view of the sleeve within the device taken along line 10—10 of FIG. 9 with the needle removed;

FIGS. 15A–15B each depict a cross-sectional side view of various disposable fiber and needle configurations for use with the device of FIG. 14;

FIG. 26 depicts the handpiece of FIG. 18 pressed against a heart wall with the needle puncturing through the heart;

FIG. 27 is a cross-sectional view of another handpiece in accordance with the present invention wherein the needle collar is secured to the handpiece housing;

FIG. 28 is a cross-sectional view of yet another handpiece having the needle collar detachably secured to the handpiece and curved at an angle of approximately thirty (30) degrees;

FIG. 29 is a further cross-sectional view of a handpiece with the needle collar detachably attached to the handpiece and curved at an angle of approximately ninety (90) degrees;

DISCLOSURE OF THE PREFERRED EMBODIMENTS

The present invention provides a surgical device for forming a channel by first utilizing mechanical energy to partially create a channel into tissue and utilizing laser energy, emitted directly onto the tissue to be vaporized, to create the remainder of the channel. The device includes a needle having a bore with an opening in communication with the bore. The needle is mechanically or manually advanced to make the first portion of the channel in the tissue. Mounted within the bore is an optical fiber for emitting the laser energy to form the remainder of the channel in the tissue.

While this invention is susceptible of embodiments in many different forms, this specification and the accompanying drawings disclose only some specific forms as examples of the invention. The invention is not intended to be limited to the embodiments so described, however. The scope of the invention is pointed out in the appended claims.

Figure 1:
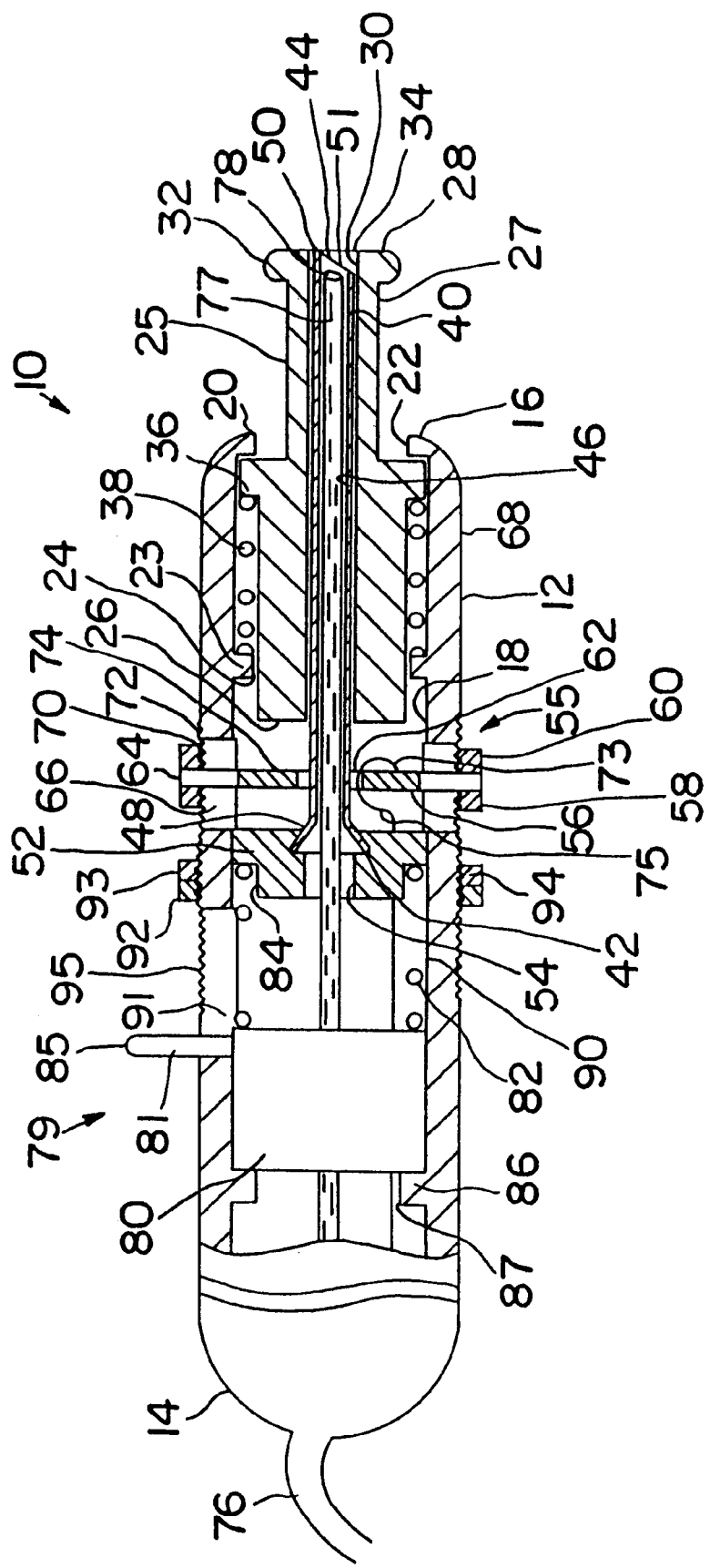
FIG. 1 is a partial cross-sectional view of a device in accordance with the present invention.

Referring to FIG. 1, a partial cross-sectional view of a device 10 in accordance with the present invention is shown. The device 10 includes a cylindrical housing 12 having a first end 14 and a tapered second end 16 with an elongated cavity 18 extending therebetween. Protruding from the tapered second end 16 and within the housing cavity 18 is a shoulder 20. The shoulder 20 is ring shaped with a circular aperture 22 in communication with the housing cavity 18.

Also extending from the housing 12 and within the housing cavity 18 is an annular abutment 23. The abutment 23 is located near the housing second end 16 and has a circular aperture 24 located at its center.

Slidably mounted within the housing cavity 18 is a hollow needle collar or guide 25 having a neck 27. The needle collar 25 is generally cylindrical in shape with an inner end 26, an outer end 28, and a bore 30 extending therebetween. The neck portion 27 of the needle collar 25 begins generally between the inner end 26 and the outer end 28 of the needle collar and extends to the outer end 28. The neck portion 27 has a smaller outer diameter than the rest of the needle collar 25.

Furthermore, the inner end 26 of the needle collar 25 extends past the aperture 24 in the housing abutment 23. Likewise, the outer end 28 of the needle collar 25 protrudes from the aperture 22 in the housing 12 and has a rounded flange 32 extending around its periphery. The rounded flange 32 results in the outer end 28 of the needle collar 25 having a flat disk shaped surface with the bore aperture 34 being located in the center.

Also extending around the needle collar 25 is a retaining ring 36. The retaining ring 36 is located between the inner end 26 and the outer end 28 of the needle collar 25 and is positioned within the housing cavity 18 between abutment 23 and shoulder 20.

Similarly, located between housing abutment 23 and the needle collar ring 36 on guide 25 is a first coiled spring 38. The coiled spring 38 wraps around the needle collar guide 25 and biases the retaining ring 36 against the housing shoulder 20 and upon compression as collar guide 25 is actuated exposes the needle 40 together with a preferably 500–1000 micron core optical fiber 77 positioned therewithin.

Slidably mounted within the needle collar bore 30 is a needle 40. The needle 40 is generally tubular in construction with a proximal end 42, a distal end 44, and a bore 46 defined therebetween. The proximal end 42 of the needle 40 may be welded or otherwise attached to wall 52 or may be flared outwardly to form a funnel 48 about which the wall may be molded. Conversely, the distal end 44 of the needle 40 is angled to form a sharp point 50 and has a bevel opening 51 in communication with the bore 46.

As shown in FIG. 1, the distal end 44 of the needle 40 remains within the collar or guide 25, but is juxtaposed to the outer end 28 of the collar. Conversely, the proximal end 42 of the needle 40 extends from the inner end 26 of the needle collar or guide 25 and into the housing cavity 18.

The wall 52 within the housing cavity 18 has a shape similar to that of a donut with a hole 54 extending through its center. The wall 52 can be made of metal or a material such as epoxy and is secured to both the housing 12 and the needle 40. Thus, the needle 40 is held by the wall 52 in a fixed position relative to the housing 12. Furthermore, as shown in FIG. 1, the open distal end of needle 40 creates an access passage for the optical fiber 77 into the needle bore 46.

Located between the wall 52 and the inner end 26 of the collar 25 is a needle adjustment means 55 for selecting a desired needle penetration depth beyond guide 25 and within tissue. In FIG. 1, the needle adjustment means 55 is shown to consist of a first movable partition 56 and two locking rings 58,60. The movable partition 56 is generally shaped like a flat washer with a hole 62 in its center and the needle 40 passing therethrough.

Radially extending from the periphery of the movable partition 56 are a plurality of support beams 64. Associated with each support beam 64 is an elongated channel 66 which extends through the housing 12 and between the wall 52 and the inner end 26 of the collar 25. Correspondingly, each channel 66 allows its associated support beam 64 to advance from the housing cavity 18 and protrude from the outside 68 of the housing 12.

The distal end of each support beam 64 protruding from the housing 12 is abutted on both sides by locking rings 58 and 60. Each locking ring 58,60 has a threaded surface which mates with complementary threads 72 located on the outside 68 of the housing 12 and about the channels 66. Thus, rotating the locking rings 58,60 causes them to move along the outside 68 of the housing 12.

Correspondingly, the first partition 56 can be moved within the housing cavity 18 by moving the rings 58,60 on the outside 68 of the housing 12. Once the partition 56 is moved to the desired location within the cavity 18, the partition is locked into place by rotating the locking rings 58,60 in opposite directions relative to each other such that they press against the support beams 64.

Mounted onto the movable partition 56 is an electrical switch 73. The switch 73 is mounted on the surface 74 of the movable partition 56 which faces the inner end 26 of the needle collar 25. The switch 73 provides a means for indicating when the desired needle penetration depth has been acquired. Correspondingly, the switch 73 is activated only when the inner end 26 of the needle collar 25 abuts against the switch.

Attached to the switch 73 is an electrical lead 75. The lead 75 provides for the transmission of signals to indicate whether the switch 73 has been activated. The electrical lead extends from the switch 73, through the hole 62 in the movable partition, and into the wall 52. The electrical lead then continues through the wall 52 and into the lead 76 extending from the housing 12. Electrical lead 75 extends to either the laser or the foot pedal switch of the laser.

Turning back to the needle 40, received within its bore 46 is an optical fiber 77. The fiber 77 is mounted within the device 10 such that the fiber can be extended from the distal end 44 of the needle 40, if desired. The optical fiber may have a thin polyamide buffer coating which allows both the fiber 77 and the needle 40 to have a small diameter.

As shown in FIG. 1, the distal end 78 of the fiber 77 is positioned such that it is located adjacent to the needle point 50 but does not protrude from the needle bore 46. Conversely, at the distal end 44 of the needle 40, the fiber 77 continues through the hole 54 in the wall 52 and into the housing cavity 18.

The portion of the fiber 77 projecting within the housing cavity 18 is connected to fiber driver means 79. In FIG. 1, the driver means 79 is shown to consist of a sleeve 80 with a lever 81. The sleeve 80 is generally cylindrical in shape and is slidably mounted within the housing cavity 18. The sleeve 80 clamps around the optical fiber 77 such that the optical path within the fiber is not obstructed. However, movement of the sleeve 80 within the housing cavity 18 results in the same movement in the fiber 77.

Located between the sleeve 80 and the wall 52 is a second coiled spring 82. The coiled spring 82 projects into a circular groove 84 around the peripheral of the wall 52 and biases the sleeve 80 against a sleeve stop abutment 86.

The stop abutment 86 protrudes from the housing 12 and within the housing cavity 18. The abutment 86 is generally annular with a circular aperture 87 located at its center.

The lever 81 extending from the sleeve 80 consists of an elongated beam member with a distal end 85. The distal end 85 of the lever 81 advances through an elongated channel 91 and protrudes from the outside 68 of the housing 12. The channel 91 in the housing 12 extends from the wall 52 and towards the first end 14 of the housing 12. The movement of the lever 81 within the channel 91 is bounded by the housing 12 on one end and a pair of locking rings 92 and 93 on the other.

Each locking ring 92,93 has a threaded surface 94 which mates with complementary threads 95 located on the outside 68 of the housing 12 and about the channel 91. Thus, rotating the locking rings 92,93 causes them to move along the outside 68 of the housing 12.

Correspondingly, the travel of the lever 81 within the channel 91 can be restricted by moving the rings 92,93 towards the first end 14 of the housing 12. Once the rings 92,93 are moved to the desired location, the rings can be locked into place by rotating the rings in opposite directions relative to each other such that they press against one another.

As indicated previously, prior to using the device 10 of FIG. 1, the needle adjustment means 55 and the actuator means 79 must be properly set such that the needle 40 and the fiber 77 will be exposed and penetrate into adjacent tissue to their desired respective depths. The needle adjustment means 55 is set by moving the partition 56 to the desired location within the housing cavity 18. The partition 56 is moved within the housing cavity 18 by releasing the locking rings 58 and 60 from against the support beams 64. Once the partition 56 is moved to the desired location within the housing cavity 18, the partition is locked into place by rotating the locking rings 58,60 in opposite directions relative to each other such that they press against the partition support beams 64.

The fiber driver means 79 is set in a similar manner to that of the needle adjustment means 55. Correspondingly, locking ring 92 is moved along the outside 68 of the housing 12 by rotating the ring. Once the ring 92 is set to the desired position, the ring is held in position by firmly rotating ring 93 against locking ring 92 and then rotating the rings in opposite directions relative to each other such that they press against one another.

Figure 2:
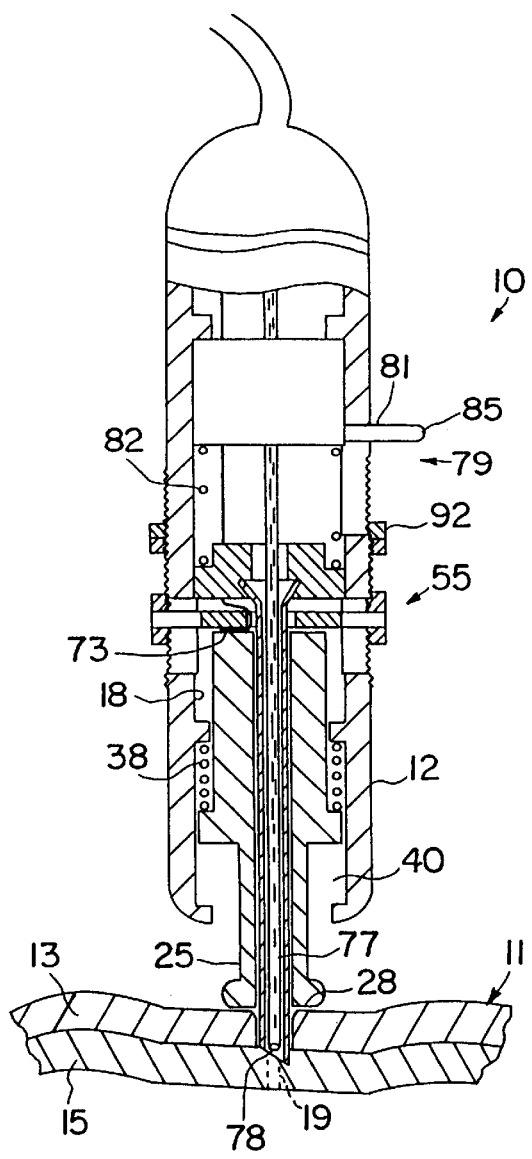
FIG. 2 is a partial cross-sectional view of the device of FIG. 1 pressed against the outer surface (epicardium) of a heart with the needle extending from the needle collar and into the epicardium.
Figure 3:
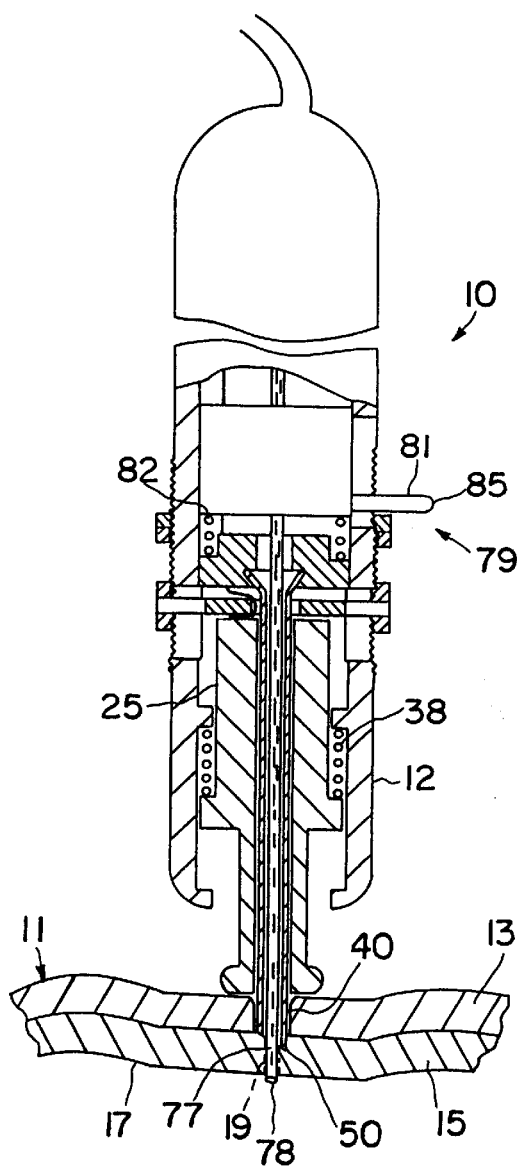
FIG. 3 is a partial cross-sectional view of the device of FIG. 2 with the fiber extending from the needle and into the inner layer (endocardium) of the heart.

Once the needle adjustment means 55 and the fiber driver means 79 are set to the desired depths, the device 10 can be used to perform surgical procedures such as transmyocardial revascularization. In such a procedure, the outer end 28 of the needle collar 25 is placed against the outer surface [i.e., epicardium] of a patient's heart. This is illustrated in FIGS. 2 and 3 where surgical device 10 is shown pressed against the epicardium 13 of a heart 11.

Once the surgical device 10 is positioned against the heart 11, advancing the housing 12 towards the heart causes the outer end 28 of the needle collar 25 to be urged against the epicardium 13 such that the needle collar retracts into the housing cavity 18 as the spring 38 compresses. As the needle collar 25 retracts into the housing cavity 18, the needle 40 extends from the needle collar and penetrates the epicardium 13. The needle 40 proceeds within the epicardium 13 until the inner end 26 of the needle collar 25 abuts against the switch 73. Abutment of the needle collar 25 against the switch 73 operates as a means for stopping both the retraction of the needle collar 25 within the housing cavity 18 and the penetration of the needle 40 into the epicardium 13. Furthermore, the switch 73 transmits a signal to the laser to indicate that the needle 40 has penetrated to the desired depth which was previously determined by setting the needle adjustment means 55 which enables the laser.

Once the needle 40 has penetrated to the desired depth within the epicardium 13, the fiber driver means 79 can be used to move the fiber 77 from the needle bore 46 further through the endocardium 15 of the heart 11. At the instant the fiber 77 proceeds to advance through the endocardium 15, the transmittal of laser energy within the fiber 77 commences and, if desired, continues until the fiber 77 is withdrawn completely from the endocardium 15. The laser energy may originate from a conventional laser which radiates laser energy into the fiber 77.

While energy from a Holmium: YAG laser or comparable laser at a wavelength of 1400 to 2200 micrometers is preferred, energy from an excimer laser (300 to 400 micrometers), argon laser (488–520 micrometers), KTP laser (532 micrometers, erbium laser (2940 micrometers), or any other source of laser energy able to be transmitted through optical fibers, pulsed, gated, or continuous wave may be utilized. The laser energy passes within the fiber 77 and is emitted from the distal end 78 of the fiber. A remote foot switch (not shown) connected to lead 75 may be provided to activate the laser if desired.

The fiber driver means 79 moves the fiber 77 from the needle and into the endocardium 15 by advancing the lever 81 towards the locking ring 92. Movement of the lever 81 causes the sleeve 80, along with the fiber 77, to proceed towards the heart 11. Furthermore, the spring 82 is compressed as the fiber 77 penetrates through the endocardium 15.

As the fiber 77 proceeds within the endocardium 15, the laser energy being emitted from the distal end 78 of the fiber vaporizes any tissue in the path of the fiber. The fiber 77 continues to penetrate through the endocardium 15 until the lever 81 abuts against ring 92. Abutment of the lever 81 against ring 92 serves as a means for indicating that the fiber 77 has penetrated to the desired depth which was previously determined by setting the actuator means 79, and thus fiber 77 is withdrawn from endocardium 15, while laser energy continues to be emitted therefrom, if desired. When fiber 77 is fully withdrawn to its initial position, the emission of laser energy ceases and the housing 12 is moved rearwardly, removing needle 40 from the epicardial tissue 13, and the needle collar is moved forward by spring 38 to its original position.

FIG. 3 provides a partial cross-sectional view of the device 10 of FIG. 2 with the fiber 77 penetrating to the desired depth such that the fiber 77 extends through the heart endocardium 15 and the inner wall 17 of the heart 11. The penetration of the fiber 77, along with the laser energy being emitted from the distal end 78 of the fiber, vaporizes tissue to form a channel 19. Confirmation that the fiber 77 has extended through the inner wall 17 of the heart 11 may be achieved by using a conventional ultrasound device to observe bubbles in the heart chamber caused by the emission of the laser energy or an acoustic sensor placed on the patient's carotid or other artery for detecting the sound of the bubbles.

Once the fiber 77 has extended through the heart inner wall 17, the transmission of laser energy within the fiber may be terminated. However, in an alternative embodiment, the transmission of laser energy may be continued until the fiber 77 has been fully retracted from the endocardium 15.

Removal of the fiber 77 is accomplished by discontinuing the application of force against the lever 81 such that the spring 82 may incite the actuator means 79 to withdraw the fiber 77 from the endocardium 15. The discontinuation of force allows the spring 82 to expand and cause the sleeve 80, along with the fiber 77, to move away from the heart 11. Retraction of the fiber 77 from within the endocardium 17 may also be assisted by applying a force away from locking ring 92 and against the lever 81.

The retraction of the fiber 77 from the newly formed channel 19 in the endocardium 15 allows blood to enter the channel from the inside of the heart 11. Once the distal end 78 of the fiber 77 is moved within the needle 40, the needle may be removed from the epicardium by moving housing 12 rearwardly. However, if laser energy was being transmitted during the withdraw of the fiber 77 from the endocardium 15, then the energy transmission may be terminated before needle 40 begins to withdraw from the epicardium 13. The determination of whether to continue the transmission of laser energy as the fiber 77 is removed from the epicardium 15 depends on if it is desirable to produce a coagulation zone about the channel through the patent's epicardium.

The needle 40 may be removed from the epicardium 13 by moving the housing 12 away from the heart 11 which causes the needle collar 25 to extend from the housing cavity 18 as the spring 38 decompresses and the switch 73 becomes deactivated. The deactivation signal transmitted by the switch 73 can be used as a means for switching the laser energy off. The device 10 can then be moved to another position on the heart's surface and the procedure repeated.

When used on a beating heart, it is desired that the above procedure take only 0.1 to 0.7 seconds, preferably 0.3 to 0.6 seconds, from the time the needle 40 begins to extend from the needle collar 25, the channel 19 is formed, and the needle is fully retracted back into the needle collar. The above procedure may be conducted over a longer period of time in an arrested heart, for example, during coronary bypass graft surgery, or in a beating heart during several beats, if desired. In any case, advancing the device 10 mechanically at a selected rate at a desired energy level enables the channels to be made with a uniform diameter and depth of coagulation zone surrounding the channel.

Figure 4:
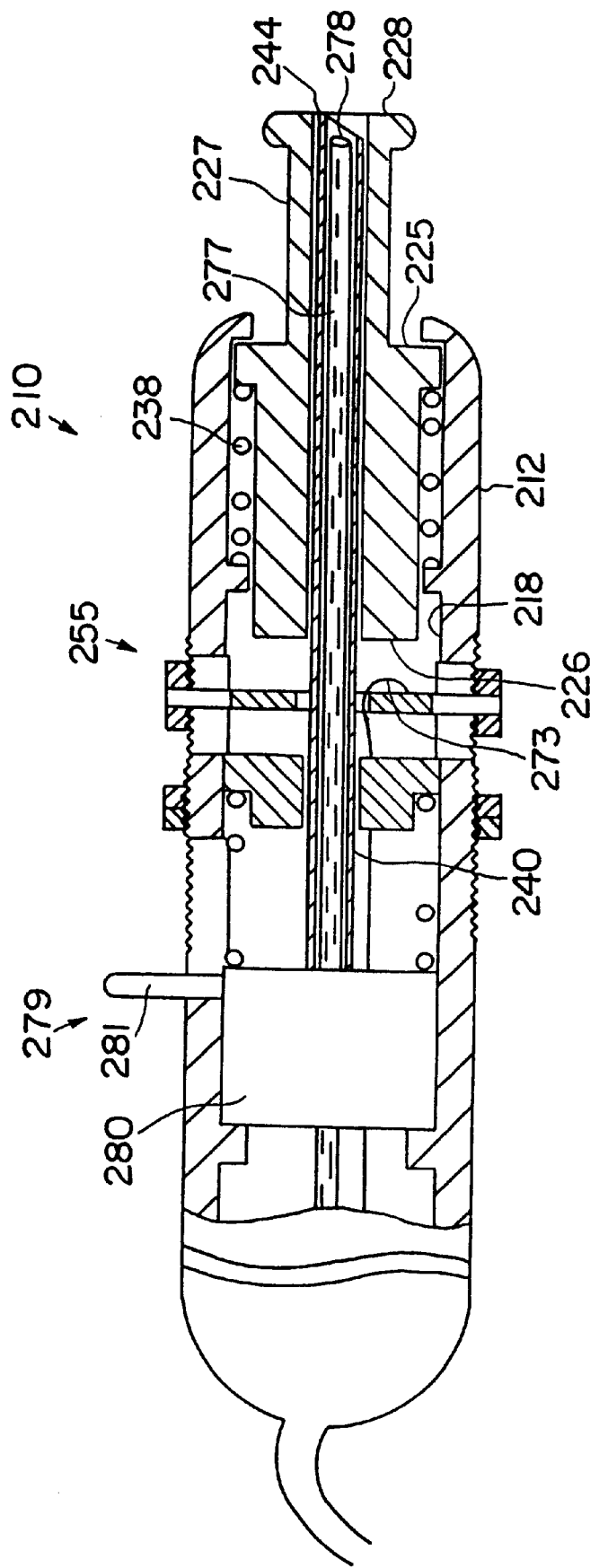
FIG. 4 is a partial cross-sectional view of another embodiment of a device in accordance with the present invention.

In another preferred embodiment the needle and the optical fiber advance together through both the epicardium and the endocardium. Turning to FIG. 4, a partial cross-sectional view of a device 210 for performing such a procedure is provided. The device 210 is similar to the device 10 depicted in FIGS. 1–3. Correspondingly, the last two digits in the 200 series of numerals depicted in FIG. 4 are connected to elements which have the same function and/or structure as those described with regard to FIGS. 1–3. In FIG. 4, however, the needle 240 is attached to the sleeve 280 which results in the optical fiber 277 being held in a fixed position relative to the needle 277.

The device 210 operates similarly to the device 10 depicted in FIGS. 1–3. Thus, prior to using the device 210, the needle adjustment means 255 and the fiber driver means 279 must be properly set, or interlocked, such that the needle 240 and fiber 277 together will penetrate to the desired depth. Once the needle adjustment means 255 and the fiber driver means 279 are set to the desired depths, the device 210 can be used in a procedure similar to that discussed above.

Correspondingly, in a transmyocardial revascularization procedure, the outer end 228 of the needle collar 225 is placed against the epicardium of a heart. The device housing 212 is then advanced towards the heart such that the needle 240 proceeds within the epicardium until the inner end 226 of the needle collar 225 abuts against the switch 273. Abutment of the needle collar 225 against the switch 273 operates as a means for stopping the penetration of the needle 240 into the epicardium and cause the switch 273 to transmit a signal indicating that the needle 240 has penetrated to the desired depth.

Once the needle 240 has penetrated to the desired depth within the epicardium, the actuator means 279 is used to move the needle 240 and the fiber 277 an additional distance through the endocardium of the heart. However, before the needle 240 and fiber 277 proceed into the endocardium., the transmittal of laser energy within the fiber 277 may be commenced such that the energy is emitted from the distal end 278 of the fiber.

The actuator means 279 moves the needle 240 and the fiber 277 an addition distance such that the laser energy being emitted from the distal end 278 of the fiber vaporizes any endocardium tissue in the path of the needle and the fiber. Once the needle 240 and the fiber 277 have traveled through the endocardium and into the heart's chamber, the transmission of laser energy within the fiber may be terminated. However, in an alternative embodiment, the transmission of laser energy may be continued until the fiber 277 and the needle 240 have been retracted from the endocardium.

The fiber 277 and the needle 240 are removed from the endocardium by discontinuing the application of force against the lever 281. The retraction of the fiber 277 and the needle 240 from the newly formed channel in the endocardium allows blood to enter the channel from the inside of the heart. Furthermore, if laser energy was being transmitted during the withdrawal of the fiber 277 and the needle 240 from the endocardium, then the energy transmission may be terminated before the fiber and needle are withdrawn into the epicardium. However, the transmission of laser energy as the fiber 277 is removed from the epicardium may be continued, if desired, to produce a thin coagulation zone about the channel through the epicardium.

Consequently, the needle 240 and fiber 277 may be removed from the epicardium by moving the housing 212 away from the heart, which causes the inner end 226 of the needle collar 225 to extend from the housing cavity 218 as the spring 238 decompresses and the switch becomes deactivated. The signal that the switch has become deactivated can be used for an indication to turn the laser off.

The above transmyocardial revascularization procedures can be used on an arrested heart during coronary bypass surgery or other open chest procedure, or on a beating heart. If used on a beating heart it is desired that the diameter of the housing, or at least the neck and the outer end of the needle collar, have a diameter as small as possible so that the device can be inserted through a trocar puncture (i.e., first port) between the ribs. Preferably the diameter is in the range of about three to ten millimeters. More preferred, however, is a diameter of about four to about six millimeters.

In addition, as indicated above, the flange of the needle collar is rounded and the second end of the housing is tapered so that the device, or at least the needle collar, can be easily inserted through a puncture between the ribs of a patient, if so desired.

A thoracoscope may also be inserted through a second port to allow visualization of the positioning of the device against the heart. Furthermore, a third port may be used for inserting a blunt instrument to press against the heart if bleeding occurs at the puncture site.

In a further embodiment it is preferred that the outer end 228 is positioned against a chest wall instead of against the heart itself. This procedure is similar to that discussed above. However, in such a case it is preferred that the needle 240 be either 14-gauge needle with a 1000 micron fiber therewithin or a 16-gauge needle with a 600 micron fiber therewithin.

In performing the procedure, the outer end 228 of the needle collar 225 is placed against the chest wall. The device housing 212 is pressed against the chest such that the needle 240 is inserted between the ribs with the distal tip 244 of the needle not quite contacting the heart when the heart is fully expanded in diastole. The positioning of the needle tip 244 relative to the heart can be observed by a thoracoscope inserted through a second port.

The needle is then advanced into the epicardium until the inner end 226 of the needle collar abuts against the switch 273. Once the needle 240 has penetrated to the desired depth within the epicardium, the actuator means 279 is used to move the needle 240 and the fiber 277 an addition distance within the endocardium of the heart. Furthermore, the transmittal of laser energy from the distal end 278 of the fiber 277 occurs as penetration of the endocardium is begun.

Once the needle 240 and the fiber 277 have penetrated through the endocardium and into the heart chamber, the transmission of laser energy within the fiber may be terminated. However, in an alternative embodiment, the transmission of laser energy may be continued until the fiber 277 and the needle 240 have been retracted from the endocardium.

The fiber 277 and the needle 240 are removed from the endocardium by discontinuing the application of force against the lever 281. Furthermore, if laser energy was being transmitted during the withdraw of the fiber 277 and the needle 240 from the endocardium, then the energy transmission may be terminated before the fiber and needle enter the epicardium, unless it is desired that laser energy be continued through the epicardium. Finally, the needle 240 and fiber 277 are removed from the epicardium by moving the housing 212 away from the heart.

It is desired that the above procedure in the case of a beating heart take only 0.1 to 0.7 seconds, preferably 0.3 to 0.6 seconds, from the time the needle 240 first punctures the heart to the time the needle leaves the heart.

In another embodiment it may be desired to have a means for indicating when the needle has advanced a preselected distance into the chest wall.

Figure 5:
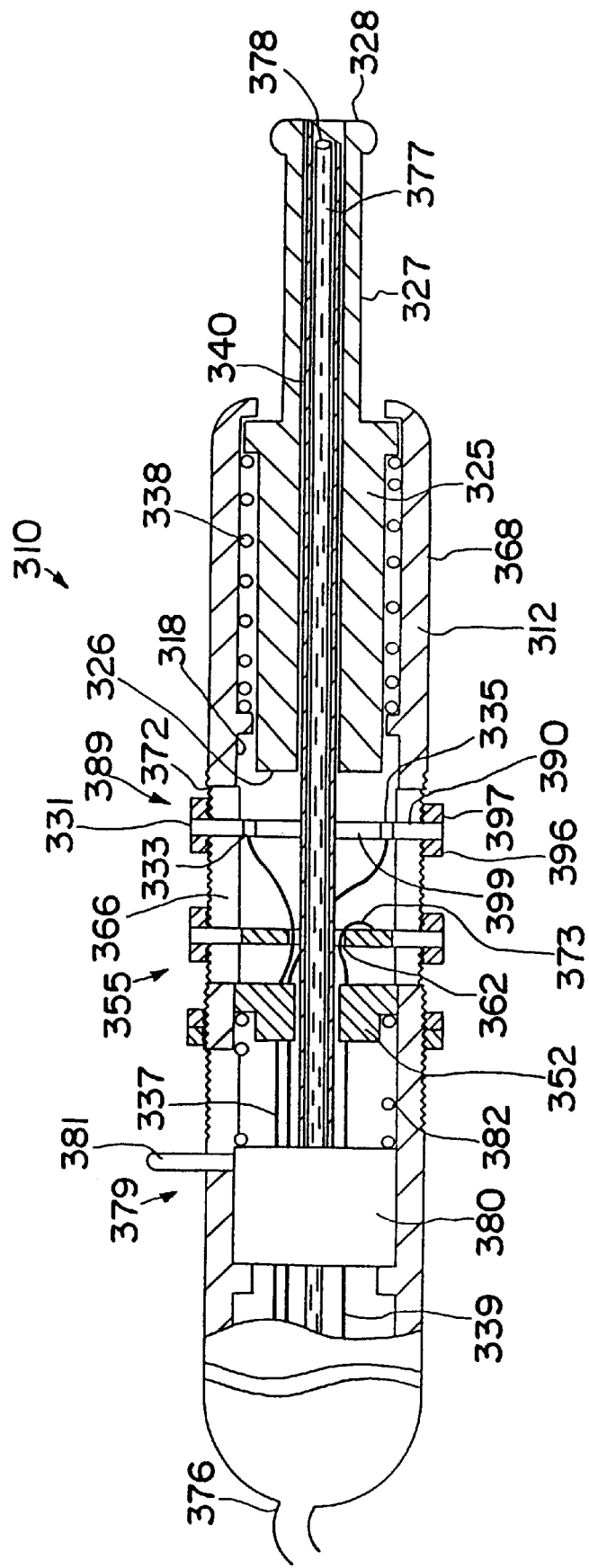
FIG. 5 is a partial cross-sectional view of yet another embodiment of a device in accordance with the present invention.

Turning to FIG. 5, a partial cross-sectional view of a device 310 for performing such a procedure is provided. The device 310 is similar to the device 210 depicted in FIG. 4. However, located between the needle adjustment means 355 and the inner end 326 of the collar 325 is an indicator means 389 for indicating the needle depth when the needle 340 has advanced a preselected distance from the outer end 328 of the collar 325 and thus into heart issue or the chest. In FIG. 5, the indicator means 389 is shown to have a second movable partition 390 and two locking rings 396,397. The movable partition 390 is generally shaped like a flat washer with an aperture 399 in its center and the needle 340 passing therethrough. The aperture 399 is large enough to allow the needle collar 325 to pass therethrough.

Radially extending from the periphery of the movable partition 390 are a plurality of support beams 331. Each support beam 331 is associated with the elongated channel 366 which extends through the housing 312 and between the wall 352 and the inner end 326 of the collar 325. Correspondingly, each channel 366 allows its associated support beam 331 to advance from the housing cavity 318 and protrude from the outside 368 of the housing 312.

The distal end of each support beam 331 protruding from the housing 312 is abutted on both sides by locking rings 396 and 397. Each locking ring 396,397 has a threaded surface which mates with the complementary threads 372 located on the outside 368 of the housing 312 and about the channels 366. Thus, rotating the locking rings 396,397 causes them to move along the outside 368 of the housing 312.

Correspondingly, the partition 390 can be moved within the housing cavity 318 by moving the rings 396,397 on the outside 368 of the housing 312. Once the partition 390 is moved to the desired location within the cavity 318, the partition is locked into place by rotating the locking rings 396,397 in opposite directions relative to each other such that they press against the support beams 331.

Mounted onto the movable partition 390 are two brush contacts 333,335. The contacts 333,335 are mounted on the movable partition 390 such that they protrude within the partition aperture 399. Therefore, the brush contacts 333,335 wipe against the needle collar 325 as the collar proceeds through the aperture 399.

In this embodiment, it is preferred that the needle collar 325 be constructed of a conductive material such that the needle collar provides a conductive path between the two brush contacts 333,335 as the collar proceeds through the aperture 399. Therefore, the brushes provide a means for indicating when the needle has reached a preselected depth because a conductive path is provided between the brushes 333,335 by the collar 325.

Attached to the contacts 333 and 335, respectively, are electrical wires 337 and 339. The wires 337,339 provide for the transmission of signals to determine whether the collar 325 is within the aperture 399 of the indicator means 389. The electrical wires extend from the brushes 333,335, through the hole 362 in the other moveable partition, and into the wall 352. The electrical wires then continue through the wall 352, the sleeve 380, and into the lead 376 extending from the housing 312.

The device 310 operates similarly to the device 210 depicted in FIG. 4. Thus, prior to using the device 310, the needle adjustment means 355 and the actuator means 379 must be properly set such that the needle 340 and the fiber 377 will penetrate to the desired depth. Furthermore, the indicator means 389 must be set by moving the partition 390 to the desired location within the housing cavity 318. The partition 390 is moved within the housing cavity 318 by releasing the locking rings 396 and 397 from against the support beams 331. Once the partition 390 is moved to the desired location within the housing cavity 318, the partition is locked into place by rotating the locking rings 396,397 in opposite directions relative to each other such that they press against the partition support beams 331.

Once the indicator means 389, the needle adjustment means 355, and the actuator means 379 are properly configured, the device 310 can be used in a procedure similar to that discussed above. Correspondingly, in a transmyocardial revascularization procedure, the outer end 328 of the needle collar 325 is placed against the chest wall. The device housing 312 is pressed against the chest such that the needle 340 is inserted between the ribs.

As the needle is inserted into the chest, the inner end 326 of the needle collar 325 advances into the partition aperture 399. Consequently, the brush contacts 333,335 wipe against the needle collar 325 as the collar proceeds through the aperture 399. Therefore, a electrical connection is formed between the brush contacts 333,335, by the needle collar 325, to indicate that the needle has protruded to the selected distance within the chest which was previously determined by the setting of the indictor means 389.

The needle is then advanced into the epicardium until the inner end 326 of the needle collar abuts against the switch 373. Once the needle 340 has penetrated to the desired depth within the epicardium, the actuator means 379 is used to move the needle 340 and the fiber 377 an addition distance into the endocardium of the heart. Furthermore, the transmittal of laser energy from the distal end 378 of the fiber 377 occurs as the endocardium is penetrated.

Once the needle 340 and the fiber 377 have penetrated through the endocardium and into the heart's chamber, the transmission of laser energy within the fiber may be terminated. However, in an alternative embodiment, the transmission of laser energy may be continued until the fiber 377 and the needle 340 have been retracted from the endocardium.

The fiber 377 and the needle 340 are removed from the endocardium by discontinuing the application of force against the lever 381. Furthermore, if laser energy was being transmitted during the withdraw of the fiber 377 and the needle 340 from the endocardium, then the energy transmission may be terminated before then fiber and needle are withdrawn from the epicardium. However, the transmission of laser energy may be continued through the epicardium if desired. Finally, the needle 340 and fiber 377 are removed from the epicardium by moving the housing 312 away from the heart.

Figure 6A:
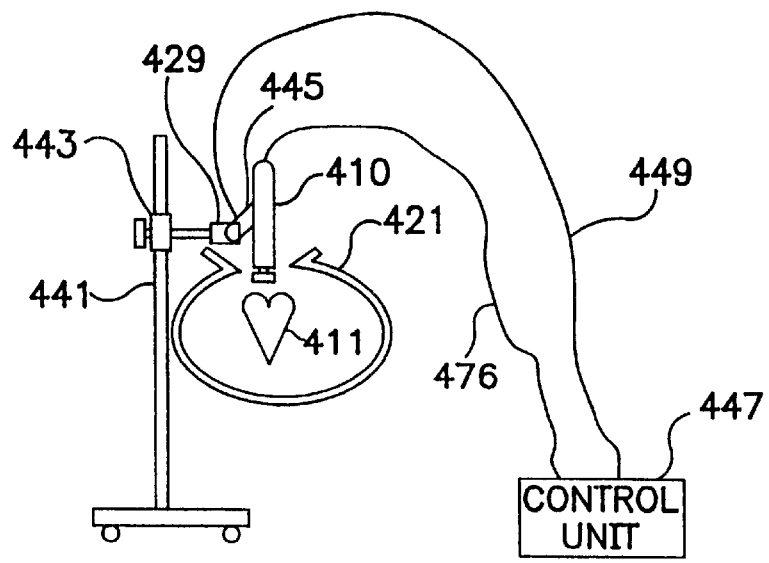
FIG. 6A is a schematic view of a mechanism for use with any of the device embodiments depicted in FIGS. 1–5 in an open chest procedure.
Figure 6B:
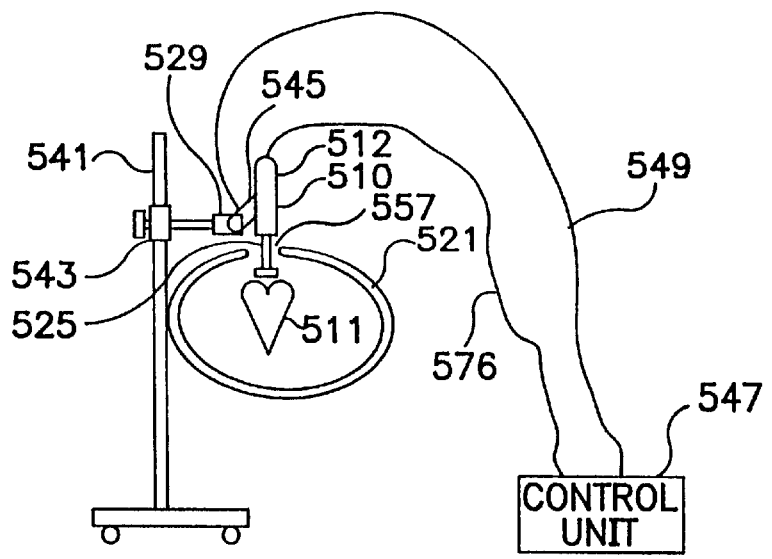
FIG. 6B is a schematic view of a mechanism for use with any of the device embodiments depicted in FIGS. 1–5 in a closed chest procedure.
Figure 6C:
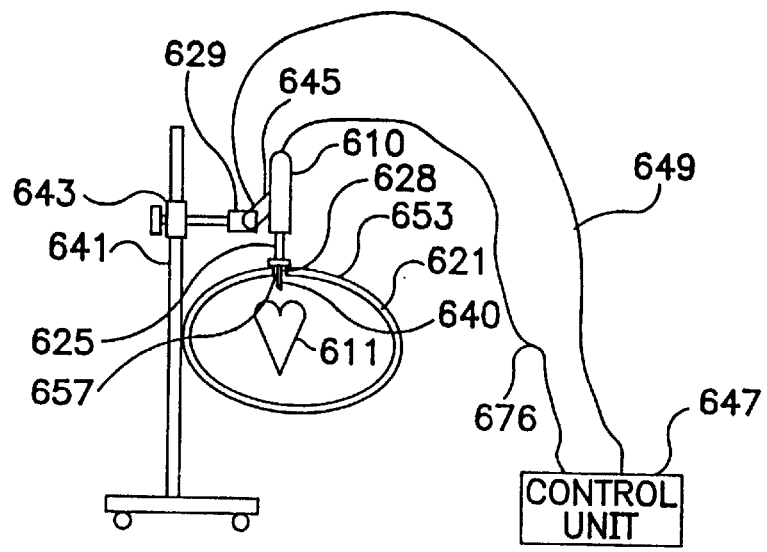
FIG. 6C is a schematic view of a mechanism for used with any of the device embodiments depicted in FIGS. 1–5 in a closed chest procedure.
Figure 7:
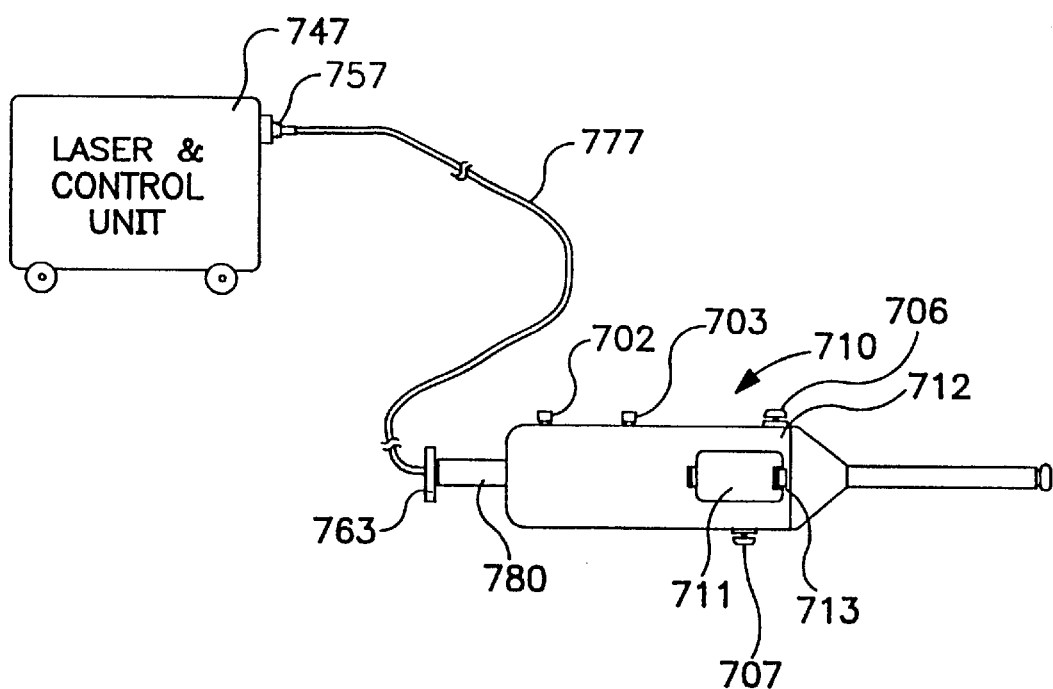
FIG. 7 is a perspective top view of another device, connected to a laser energy source, that embodies the present invention and includes a door for accessing a disposable needle.
Figure 8:
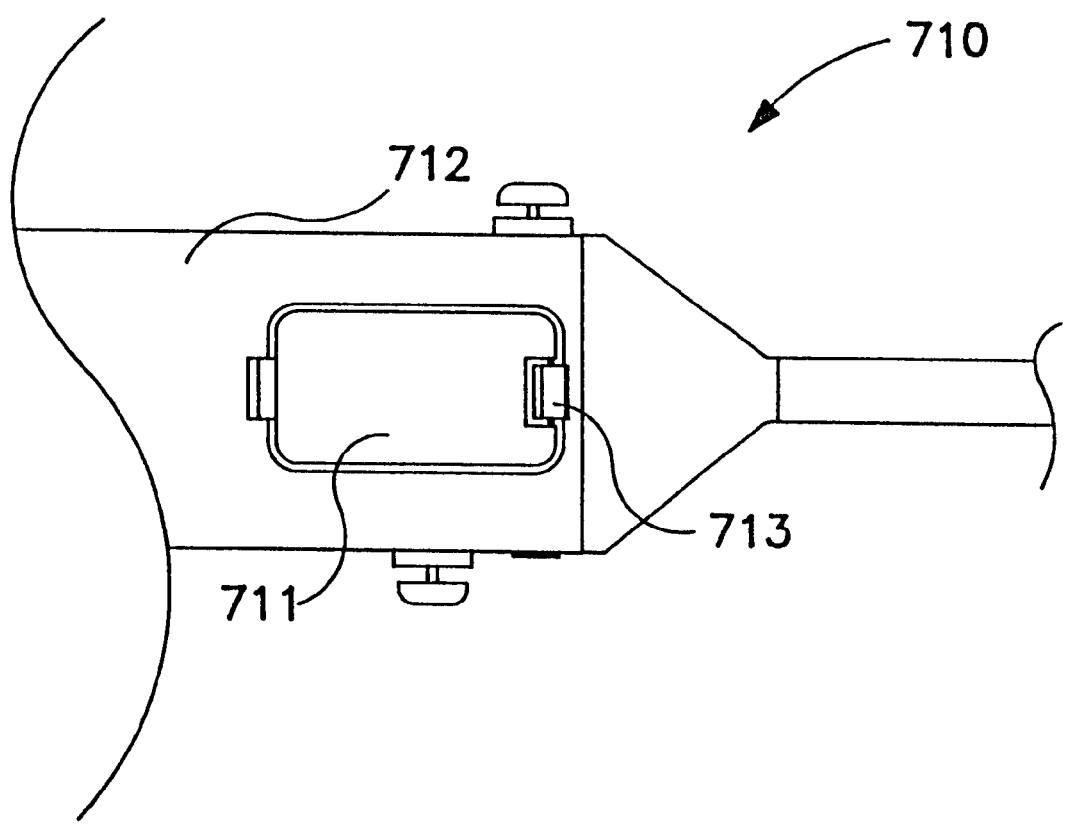
FIG. 8 is an enlarged partial top view of the device of FIG. 7 illustrating the door to access the disposable needle.

It should be noted that in all of the embodiments depicted above, the devices can be manually applied or a mechanism can be attached for operating the devices. FIGS. 6A, 6B, and 6C provide schematic views of various mechanisms for operating a device.

In FIG. 6A, the device 410 may be in accordance with any of the embodiments depicted above. The mechanism 429 is mounted on a movable platform 441 such as an I.V. pole or any other conventional structure. The mechanism 429 is adjustable connected to the pole 441, by a clamp 443, such that the mechanism is positioned at a desired height over the patient's heart 411 with the chest opened.

The mechanism 429 has an arm 445 connected directly to the device 410. The arm 445 may have air pistons, stepper motors or other devices for advancing the housing and/or fiber.

The lead 476 extending from the device 410, which contains the optical fiber and the device signal leads, is connected to the control unit 447. The control unit 447 receives position signals from the device 410 and, when commanded, transmits laser energy into the optical fiber.

It is preferred that the control unit 447 be capable of supplying laser energy at various selectable energy rates. Correspondingly, the uniform rate of penetration by the needle and/or fiber within the heart tissue correlates to the preselected laser energy rate such that, the higher the selected energy rate, the faster the penetration rate.

Accordingly, the control unit also has a wire harness 476 connected to the mechanism 429 for supplying power and controlling the advancement of the device housing and/or fiber.

Turning to FIG. 6B, another embodiment is depicted which is identical to that of FIG. 6A except that the mechanism 529 is positioned over a puncture 557 which provides access to the patient's heart 511. The puncture 557 is between the ribs of the patient and provides for the needle collar 525 to extend within the patient's chest 521 and abut against the outer surface of the heart 511. Preferably, the needle collar 525 is of sufficient length such that housing 512 remains outside of the patient's chest 521 as the needle and/or fiber are advanced into the heart 511 to form a channel.

FIG. 6C provides yet another embodiment that is similar to FIG. 6B except that the outer end 628 of the needle collar 625 abuts against the outside wall 653 of the patient's chest 621 with the needle 640 penetrating within the chest puncture 657.

In yet another embodiment, the mechanism within FIGS. 6A, 6B, or 6C can be attached to the device such that a single thrust of the arm towards the heart operates the device. For example, turning to FIGS. 5 and 6C, the arm 645 can be connected only to the lever 381 of the actuator means 379. Correspondingly, the movement of the arm 645 towards the heart 611 results in the outer end 628 of the needle collar 625 be pressed against the chest of a patient.

As the arm 645 continues to move towards the heart, the needle 340 advances within the chest puncture 657 and then into the heart since, in this embodiment, the needle collar spring 338 requires less force to compress than the actuator spring 338. Thus, the inner end 326 of the needle collar 325 moves until it abuts against the switch 373 and thus indicates that the needle 340 has penetrated to a desired depth in the heart.

Once the needle 340 has penetrated to the desired depth, the actuator means 379 moves both the needle 340 and the fiber 377 an additional distance within the heart as the spring 382 begins to compress and laser energy is emitted from the distal end 378 of the fiber.

The needle 340 and the fiber 377 are removed from the heart by moving the arm 645 away from the heart which first causes the needle and the fiber to retract from the endocardium and then from the epicardium because of the difference in the compression forces between springs 338 and 382.

It should be noted with regard to all of the embodiments depicted above that the laser can be activated by a foot-pedal, finger-button, or the "r" wave of the patient's ECG which supplies activation signals to the control unit. Likewise, the movement of the mechanism arm can be activated by a foot-pedal, finger-button, or the "r" wave of the patient's ECG.

In another embodiment, it may be advantageous to actuate the device by using compressed air. FIGS. 7–11 depict such an apparatus which also includes a disposable needle. Correspondingly, where appropriate, the last two digits in the 700 series of numerals depicted in FIGS. 7–11 are connected to elements which have the same function and/or structure as those described with regard to FIGS. 1, 4, 5, and 6.

The device 710 includes a generally rectangular door 711 that is hinged onto the device housing 712. The door 711 includes a conventional clip or latch 713, opposite the hinge, for securing the door 711 over an aperture which is in communication with the housing cavity 718.

As shown in FIG. 9, the door 711 also includes a resilient guide 721 which extends from the interior surface 729 of the door. The guide 721 includes a stem 741 which extends generally perpendicular from the door 711 with a foot 743 that outwardly projects from the distal end of the stem. Preferably, the foot 743 has an extended portion 745 that slopes away from the door interior 729 and is contoured to press against the needle as explained, in detail, below.

Figure 11:
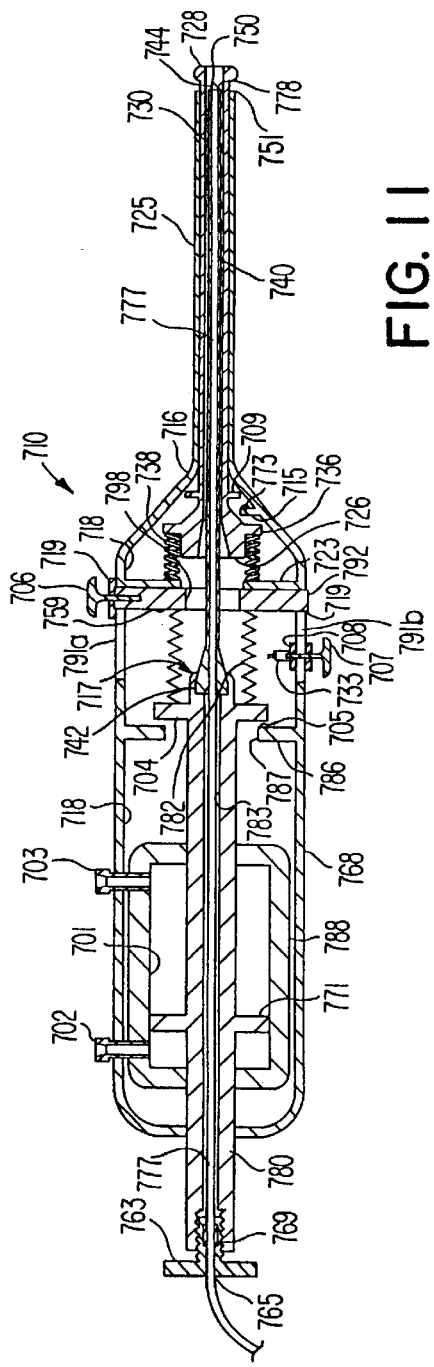
FIG. 11 is a cross-sectional top view of the device depicted in FIGS. 7–10.

FIGS. 9, 10, and 11 depict one end of the sleeve 780 within the device 710 having a socket or grip 717 for detachably connecting the sleeve 780 to the needle 740. The grip 717 includes a planar annular face 749 with an arcuate, generally semicircular, lip 753 perpendicularly projecting from the outer margin of the face. Preferably, the lip 753 is concave when view from the door 741 and has an inwardly sloped distal portion 761.

By placing the first end 742 of the needle 740 against sleeve face 749, the lip 753 adjoins against the outwardly flared proximal end 742 of the needle 740. Thus, the lip 753 receives and partially engages the needle 740.

When fiber 777 is not extending within the needle bore 746, the needle 740 is removed from the device 710 by opening the door 711 and extracting the needle. As the first end 742 of the needle 740 is pulled from the housing cavity 728, the second end 744 of the needle first vacates the needle collar bore 730 in addition to the device cavity 718.

Conversely, the needle 740 is inserted within the device 710 by opening the door 711 and inserting the second end 744 of the needle within the device cavity 728. Preferably, the needle collar bore opening within the device cavity 728 is funnel shaped for ease in inserting the needle 740 into the collar 725. The second end 744 of the needle 740 is advanced within the needle collar bore 730 until the first end 726 of the needle is allowed to adjoin against the face 749 of the sleeve 780.

Preferably, the inner diameter of the needle bore 746 has approximately a 1.5 to 2.0 millimeter diameter which allows for a 500 to 1000 micron core fiber to be positioned within the bore.

As shown in FIG. 11, sleeve 780 is longitudinally axially aligned and spaced from the needle collar 725. Accordingly, while inserting and removing the needle 740 from the device 710, the needle must be angled into the device cavity 718 between the sleeve 780 and needle collar 725. As such, it is preferred that the needle 740 allow for resilient flexing while it is both inserted and removed from the needle collar first end 726 within device 710.

As stated above, the semicircular lip 753 of grip 717 adjoins against the outwardly flared proximal end 742 of the needle 740 when the needle is installed within the device 710. The lip 753 and the guide foot 743 forms a socket 717 for coupling the needle 740 to the sleeve 780 by closing the door 741 such that the foot 743 of guide 721 adjoins against the flared portion 742 of the needle.

With the needle 740 secured by the grip 717 to sleeve 780, the sleeve face 749 pushes the needle second end 744 from the needle collar bore 730 when the sleeve is advanced towards the needle collar 725. Further, because the guide 721 is positionally fixed relative to the device housing 712 but the needle 740 is not, it is preferred that the extended portion 745 of foot 743 resiliently flex in order to allow the needle first end 742 to advance towards the needle collar 725 while the guide remains at its fixed position. Further, the length of the foot 745 should be greater than the distance traveled by the needle first end 726 so that a socket 717 is always provided for continuously securing the needle to the sleeve 780 as the needle 740 is advanced and retracted.

The fiber 777 is coupled by a conventional optical fiber connector 757 to a laser source 747 and attaches, via a threaded fiber lock 763, to the distal end of sleeve 780. The fiber 777 longitudinally extends through bore 783 in sleeve 780 and into needle bore 746. Preferably, the second end 778 of the fiber 777 is positioned within the needle bore 746 such that the fiber is located adjacent to the needle point 750, but does not protrude from the needle bore.

The threaded fiber lock 763 provides for selectably adjusting the distance between the fiber distal end 778 and the second end 744 of needle 740. The fiber lock 763 threadably engages the distal end of sleeve 780 and has an open bore 765 in communication with the sleeve bore 783.

The fiber lock 763 also includes a tubular compression fitting 769 positioned within the fiber lock bore 765. The fiber 777 extends through the fiber lock bore 765 and compression fitting 769. The fiber lock 763 secures the position of the fiber 777 within the needle bore 746 by screwing the fiber lock into the sleeve bore 783 such that the compression fitting 769 tightens around, and thus secures, the fiber. Accordingly, the distance between the fiber distal end 778 and the second end 744 of needle 740 is fixably selectable by loosening the compression fitting 769, moving the fiber 777 to the desired position, and tightening the compression fitting.

As shown in FIG. 11, radially outwardly extending from the sleeve 780 is a flange or piston 771. Preferably, the piston 771 and the sleeve 780 are of unitary construction.

The piston 771 is slidably positionable within an actuator device such as cylinder 788 which has a generally cylindrical chamber 701. The cylinder 788 is secured by conventional means to the housing 712 within cavity 718. The sleeve 780 slidably extends through the cylinder 788 with the piston 771 located in the chamber 701.

Attached to the cylinder 788 and extending from the outside of the housing 712 are tubular ports 702 and 703 which are in fluid communication with the cylinder chamber 701. The ports 702,703 are generally coupled at each longitudinal end of the cylinder chamber 701. The ports 702, 703 provide for a fluid medium, preferably air, to ingress and egress from the chamber 701.

Between the piston 771 and the sleeve grip face 717 is a shoulder flange 704 for limiting the travel of the sleeve 780 within the housing cavity 718. Preferably, the'shoulder flange 704 and the sleeve 780 are of unitary construction with the shoulder flange radially outwardly extending from the sleeve 780.

The travel of the shoulder flange 704 within the housing cavity 718, and thus sleeve 780, is bounded by wall 786 and movable partition 792. Wall 786 generally radially inwardly extends from the housing 712 into cavity 718. The wall 786 only partially extends into the housing cavity 718 to form an aperture 787 having an inner diameter which is less than the outer diameter of the shoulder flange 704. Thus, the shoulder flange 704 cannot pass through the aperture 787 in wall 786.

Attached to the wall 786 proximate to aperture 787 and facing the shoulder flange 704 is switch 705 for indicating when the sleeve 780, and thus the needle 740, is retracted. Preferably, switch 705 is activated when it is abutted by shoulder flange 704.

Moveable partition 792 also radially inwardly extends within the housing cavity 718. An aperture 798 is located generally in the center of the partition 792 with the sleeve 780 passing therethrough. Further, radially extending from the periphery of the movable partition 792 are a plurality of support beams 719. Associated with each support beam 719 is an elongated channel 791a,b which extends through the housing 712 and between the wall 786 and annular abutment 723. Correspondingly, each channel 791a,b allows its associated support beam 719 to advance from the housing cavity 718 to a position generally flush with the outside 768 of the housing 712.

Attached to partition 792 is a locking member comprising a set screw 706 for adjustably fixing the moveable partition to the housing 712. Preferably, the set screw 706 is threadably secured to the movable partition 792 and extends from the partition, to the outside 768 of the housing 712, via elongated channel 791a. As such, the position of the partition 792 is adjusted by releasing set screw 706, moving the partition to the desired location within the housing cavity 718, and tightening the set screw.

Also attached to partition 792 proximate to aperture 798 and facing the shoulder flange 704 is switch 759 for indicating when the sleeve 780, and thus the needle 740, is fully extended from the device 710. Preferably, switch 759 is activated when it is abutted by shoulder flange 704.

Extending along elongated channel 791b is a set screw 707 and clamp assembly 708 for adjustable moving a sensor 733 within the housing cavity 718. The clamp assembly 708 abuts against both the inside 718 and the outside 768 of the housing 712 with the set screw 707 extending through the channel 791b and threadably secured to the clamp assembly.

Sensor 733 is attached to the clamp 708 within the housing cavity 718. The sensor 733 detects when the sleeve 780, and thus the needle 740, has traveled a predetermined fixed distance. As such, the sensor 733 projects a distance within the housing cavity 718 that is generally equal to the distance between the housing 712 and the periphery of shoulder flange 704.

The set screw 707 allows for both adjustably securing the clamp 708 to, and releasing it from, the housing 712. Correspondingly, positioning of the clamp 708 results in like placement of the sensor 733 within the housing cavity 718. The sensor 733 is activated, preferably, when it comes in contact with, or is brushed by, the shoulder flange 704.

Radially outwardly extending from the needle collar 725 and within the housing cavity 718 is a stop flange 709. Further, a post 715 extends within the housing cavity 718 to limit the travel of the needle collar 725 to between the post 715 and the tapered second end 716 of the housing 712.

Mounted on the distal end of post 715 and facing towards the stop flange 709 is switch 773 for detecting when the needle collar 725 has been pushed a fixed distance within the housing cavity 718.

As indicated above, before the device 710 is used for forming a channel within tissue, the distal end 778 of fiber 777 is inserted through the bore 765 of compression fitting 769. The fiber 777 proceeds through the fiber lock 763 and the sleeve bore 783 such that the fiber is finally positioned within the needle bore 746.

Preferably, the distal end 778 of the fiber 777 is positioned proximate to the needle opening 751. Fiber lock 763 is tightened to maintain the position of the distal end 778 of the fiber 777 relative to the needle opening 751.

In a procedure where the heart has been arrested, device 710 is preferably used with an excimer laser for controllably emitting substantially non-thermal laser energy from the distal end 778 of fiber 777. In a procedure where the heart is beating, a laser generating a greater amount of energy is desired.

Before use, the laser 747 is set to deliver a desired amount of energy. The laser 747 is enabled to generate laser energy by depressing a footswitch or the like. However, it is desired that no laser energy be transmitted into the fiber 777, and thus emitted from the fiber distal end 778, until sensor 733 is activated as explained, in detail, further herein.

Preferably, in a procedure where the heart has been arrested, device 710 is positioned by hand such that the second end 728 of the needle collar 725 evenly contacts the outer surface of the heart. The housing 712 of the device 710 is then manually pressed towards the heart such that the needle collar 725 retracts within the housing cavity 718 as springs 738 compress.

The advancement of the needle collar 725 into the housing cavity 718 is terminated by stop flange 709 abutting against, and thus activating, switch 773. Compressed air, provided by a conventional air pump (not shown), is injected into forward air inlet port 702 by the activation of switch 773. The compressed air enters the cylinder chamber 701 and forces against piston 771 such that the piston, and thus sleeve 780, are advanced towards partition 792 and springs 782 are compressed between flange 704 and partition 792. Preferably, the compressed air forces the sleeve 780 to advance at a preselected velocity of about one (1) to three (3) millimeters per second.

As the sleeve 780 advances, attached needle 740 and fiber 777 are advanced a desired distance, preferably approximately one third (⅓) of the way through the heart wall, when sensor 733 is activated by contacting with shoulder flange 704. The position of the sensor 733 is preset by using ultrasound imaging or the like to estimate the thickness of the heart wall.

Sensor 733 is activated when it comes in contact with the shoulder flange 704. In response to activation of sensor 733, the laser unit 747 transmits laser energy through fiber 777 which is emitted from the fiber distal end 778. The fiber 777 and the needle 740 continue to advance together, preferably, through the heart wall. As such, it is desired that the needle 740 and fiber 777 are capable of fully traversing through a heart wall having a thickness from about 1.5 to 3.5 centimeters and into the heart chamber by about 0.2 to 0.5 centimeters.

The needle 740 and fiber 777 pass through the heart wall at the chosen rate of speed until shoulder flange 704 contacts, and thus actives, reserving microswitch 759. The switch 759 is operably connected to the control unit 747 which detects when the switch has been activated. In response to the switch activation, the control unit 747 terminates the injection of air into forward air inlet port 702 and injects air into reverse air inlet port 703.

The compressed air enters the cylinder chamber 701 and forces against piston 771 such that the piston, and thus sleeve 780, are advanced away from partition 792 and springs 782 are allowed to decompress. As such, needle 740 and fiber 777 are withdrawn from the heart wall.

During the withdraw, shoulder flange 704 brushes against switch 733 which commands the control unit 747 to stop the transmission of laser energy through the fiber 777 and emanating from the fiber distal end 778.

The travel of the needle 740 and fiber 777 back into needle collar 725 is stopped when shoulder flange 704 adjoins against microswitch 705. Further, the control unit 747, which is operably connected to microswitch 705, stops the injection of air into reverse air inlet port 703 when the flange 704 adjoins against switch 705.

Device 710 is then lifted off the heart wall which results in the needle collar 725 resuming its original position wherein springs 738 resiliently press stop flange 709 against the tapered second end 716 of device housing 712. The device 710 is then repositioned to another location on the heart's surface and the channel making process is began again.

As will be appreciated by those skilled in the art, device 710 may be mechanically advanced by means other than an air piston, such as a stepper motor or other mechanical means known in the art. However, it is preferred that the rate of advancement be selectable by either mechanical means or by entering a selected rate into a computer/controller as described, in detail, below.

As known by those skilled in the art, conventional holmium lasers have a "ramp-up" time of up to 1 second or longer from the time the laser medium is stimulated to produce laser energy until the time when laser energy is actually provided. Thus, it is desired that if device 710 is used with a conventional holmium laser during surgery, then the delivery of laser energy into fiber 777 should be gated in the manner illustrated by FIG. 12 to allow the transfer of laser energy into the fiber as soon as commanded.

Figure 12:
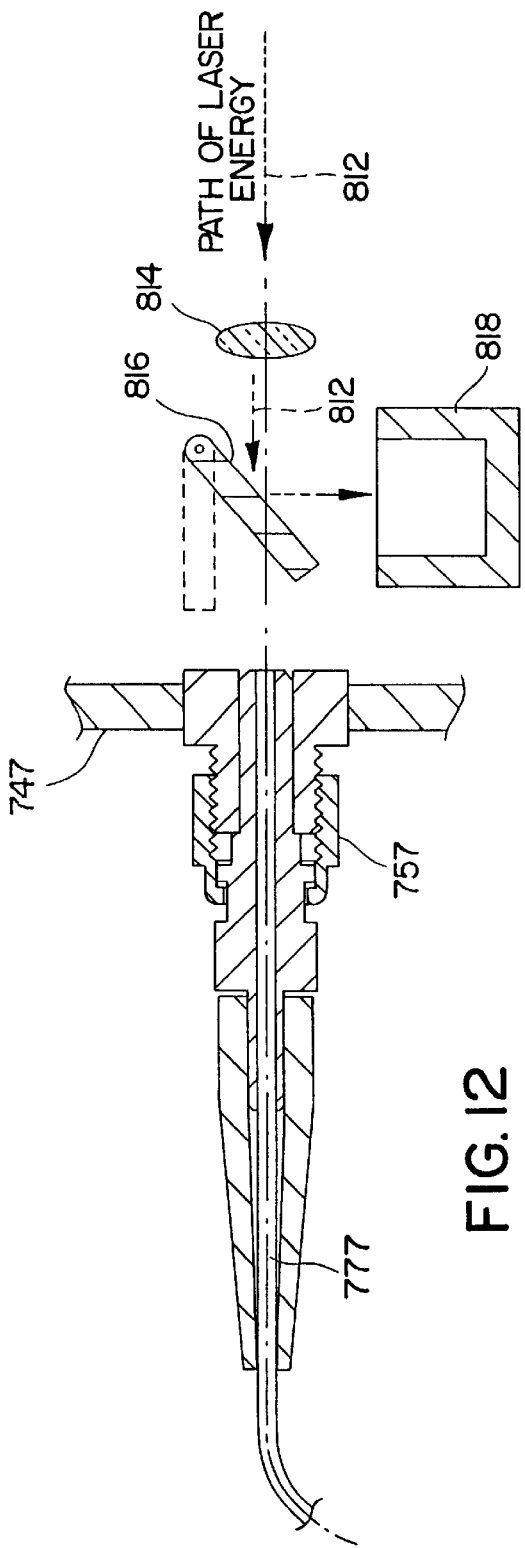
FIG. 12 is a partial schematic view of a method for gating laser energy by using a shutter having a first position, shown in phantom, and a second position, so that laser energy is continuously available for transmission without delay.

In FIG. 12, a beam 812 of laser energy is provided from a laser source 747. Such a beam of holmium laser energy can be provided by any conventional means known in the art such as that disclosed by U.S. Pat. No. 5,387,211, issued to Saadatmanesh et al., and incorporated herein by reference.

The laser energy beam 812 is received by a conventional focusing element such as a lens 814. The laser energy 812 passes through the lens and is focused onto the proximal end of the optical fiber 777.

Positioned between the fiber 777 and the lens 814 is a shutter or mirror 816 for intermittently redirecting the laser energy 812 passing through the lens 814. The mirror 816 is actuated by conventional means (not shown) to one of two positions.

In the first position, the mirror 816 is positioned out of the path of the laser energy so that the energy in received into fiber 777. Conversely, in the second position, the mirror 816 is positioned in the path of the laser energy to prevent the laser energy from being received by the fiber 777. In the second position, the laser energy is reflected by the mirror 816 into a conventional beam dump 818.

Preferably, the laser source is activated to emit laser energy by depressing a foot switch or other switching device. Activation of the laser source results in the laser energy beam 812 being provided after a sufficient "ramp-time" has elapsed and prior to the commencement of the channel making process. During this time, mirror 816 is in its second position, diverting the laser beam into the beam dump 818.

When the emission of laser energy into fiber 777 is desired, the mirror 816 moves into its first position and allows for the virtually undelayed delivery of laser energy into the fiber by moving the mirror 816 out of path of the laser energy. Thus, there is no need to wait for a prolonged "ramp-up" time because the laser energy is continuously available for transmission into the fiber 777.

Using the embodiment of FIG. 11 for illustrative purposes, when shoulder flange 704 activates microswitch 733, the mirror 816 is moved out of the beam path 812 of FIG. 12 and laser energy is transmitted through fiber 777. Conversely, when shoulder flange 704 contacts microswitch 759, the mirror 816 is moved into the beam path 812 which ceases the emission of laser energy into fiber 777.

In another embodiment, it is preferred that the shutter 816 consists of a beam dump such that, instead of reflecting laser energy, the shutter is capable of absorbing the laser energy when moved into the path of the laser energy.

The present invention can be used with the heart arrested or beating. If the heart is arrested, however, to assure uniformity of the channel and the surrounding coagulation zone, the elapsed time and the amount of laser energy emitted for each channel should be the same.

If the heart is beating, then it is desired that the device 710 be positioned so that the second end 728 of needle collar 725 is close to touching the surface of the heart when the heart is fully expanded. The device is then pressed against the heart such that springs 738 are compressed and stop flange 709 abuts against, and thus activates, switch 773. In response to switch 773 being activated, the control unit 747 is enabled to control the entry and withdraw of the needle 740 and fiber 777 within the heart.

It is desired that the control unit 747 monitor the heart by a conventional ECG sensing means to control the operation of the device 710 by using a signal recognition and timing procedure similar to that disclosed by U.S. Pat. No. 4,788,975, issued to Shturman et al., and incorporated herein by reference.

Preferably, the heart is in diastole when the device 710 forms a channel within the heart by injecting and withdrawing the needle 740. It is desired that the control unit 747 determine when to form the channel in the heart by interposing an appropriate delay time from the "r" wave of the patient's ECG, taking care to avoid activation of the device in the event of a premature ventricular contraction or any other unusual variation in heart rhythm.

Forming the channel when the heart is in diastole is preferred because, at that moment, the electrical activity of the heart is least affected by the trauma of the entry of the needle 740 and the emission of laser energy. Also, the heart chamber is full of blood and the heart wall is at its thinnest.

The present invention may be positioned within the chest by placing the device 710 through a puncture between the ribs of the patient. To ensure that the device 710 is properly positioned in relation to the heart, the surgeon can observe the second end 728 of the needle collar 725 by placing an endoscope through a second puncture within the chest wall and either between the ribs or from beneath the rib cage.

Figure 13:
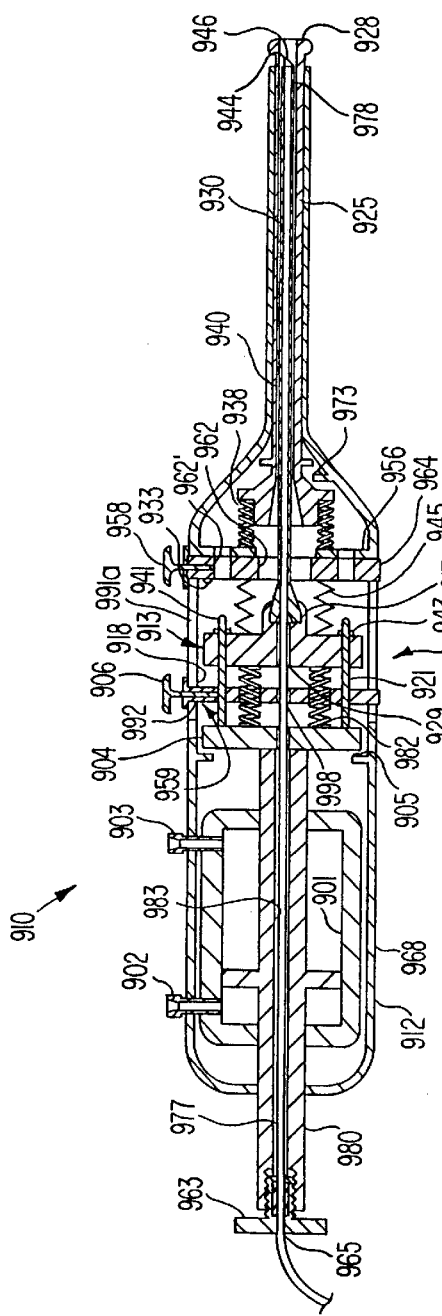
FIG. 13 is a cross-sectional top view of another device in accordance with the present invention.

FIG. 13 depicts an embodiment of the present invention which provides for advancing the needle and fiber together, and then advancing the distal end of the fiber from the needle. Correspondingly, where appropriate, the last two digits in the 900 series of numerals depicted in FIG. 13 are connected to elements which have the same function and/or structure as those described with regard to FIGS. 1, 4, 5, and 11.

In FIG. 13, the sleeve 980 has a compression coupling 911 extending from the shoulder flange 904. The compression coupling 911 includes a needle attachment 913 and springs 982.

The needle attachment 913 provides grip 917 mounted to a generally disk shaped retaining member 921. Preferably, the needle attachment 913 is of unitary construction with an open bore 929 that passes through the retaining member 921 and grip 917. The open bore 929 also is in longitudinal axial alignment with the needle collar bore 930 and the sleeve bore 983.

The grip 917 of the needle attachment 913 provides for removably connecting the needle 940 to the coupling. Further, the retaining member 921 allows for separately controlling the advancement of the needle 940 from that of the fiber 977.

The retaining member 921 is slidably mounted to guide posts 941 extending perpendicularly from the sleeve flange 904. The guide posts 941 slidably pass through the retaining member 921 with fasteners 943 attached to their distal ends to keep the retaining member from sliding off the posts.

Adjustably positionable between the retaining member 921 and the sleeve flange 904 is movable partition 992 for preselecting the desired depth that the needle 940 and the fiber 977 are to penetrate within tissue before the fiber distal end 978 advances from the needle bore 946. Aperture 998 is located generally in the center of the partition 992 with the fiber 977 passing therethrough.

Attached to partition 992 is set screw 906 for adjustably fixing the moveable partition to the housing 912. The set screw 706 extends from the partition 992, to the outside 968 of the housing 912, via elongated channel 991a. The position of the partition 992, and thus the distance the fiber 977 and needle 940 travel together, is preselected by securing the partition to the desired location within the housing cavity 718.

Mounted to the sleeve flange 904 and the retaining member 921 are springs 982 which unobtrusively pass through apertures in moveable partition 992. The springs 982 resiliently push retaining member 921 away from the sleeve flange 904 and against fasteners 943.

Also attached to partition 992 and facing shoulder flange 904 is switch 959 for indicating when the fiber distal end 978 is fully extended from the needle bore 946 by a preselected distance. The switch 959 is activated when it is abutted by shoulder flange 904 which also stops the extension of the fiber distal end 978 from the needle bore 946. As such, adjusting the position of the moveable partition 992 within housing cavity 918 establishes the distance that the fiber distal end 978 will extend from the bore 947.

Located between retaining member 921 and annular abutment 23 is a moveable partition 956 for selecting a desired needle penetration depth beyond the second end 928 of needle collar 925. The movable partition 956 is generally shaped like a flat washer with a hole 962 in its center and the needle 940 passing therethrough.

Radially extending from the periphery of the movable partition 956 are a plurality of support beams 964 which extend within channels 991. Each support beam is generally flush with the outside 968 of the housing 912.

Attached to moveable partition 956 is a locking member comprising set screw 958 for adjustably fixing the position of the partition. The set screw 958 is threadably secured to the movable partition 956 and extends onto the outside 968 of the housing 712. The position of the partition 956 is adjusted by releasing set screw 958, moving the partition to the desired location within the housing cavity 718, and tightening the set screw.

Mounted to the moveable partition 956 and the retaining member 921 are springs 945 which resiliently push the retaining member away from the partition. Preferably, however, springs 982 apply more force to press the retaining member 921 towards partition 956 than springs 945 apply to press the retaining member away from partition 956.

Extending through moveable partition 956 and annular abutment 923 are a plurality of bores 962' wherein each bore is in longitudinal axial alignment with one of the guide posts 941. The bores 962' allow the guide posts 941 to unobstructively pass through partition 956 and abutment 923 when the sleeve flange 904 is advanced towards the partition.

Mounted onto partition 956 and facing the retaining member 921 is switch 933 for detecting when the retaining member, and thus the needle 740, has traveled a predetermined fixed distance with the needle second end 944 protruding from the needle collar bore 930. Preferably, switch 933 is activated when it is abutted by retaining member 921.

As stated above, the device 910 of FIG. 13, is constructed so that needle 940 and fiber 977 may advanced together to a preselected distance within the epicardium of a heart. Thereafter, fiber 977, alone, may be advanced through the endocardium.

As the fiber 977 is withdrawn from the endocardium, laser energy is being emitted from the fiber distal end 978 until the fiber distal end is extracted back into the need bore 946. After which, the emission of laser energy ceases and needle 940 and fiber 977 are retracted together from the epicardium.

The sleeve 980, and thus the needle 940, is advanced by infusing air into forward air inlet 902. The air pushes the piston 971 and attached sleeve 980 such that springs 945 compress while springs 982 remain substantially decompressed.

As the sleeve 980 advances, the retaining member 921 abuts against switch 933 which stops the travel of the needle 940 from the needle collar bore 930. Further the laser unit is enabled to begin transmitting laser energy which is emitted from the distal end 978 of fiber 977.

As sleeve 980 continues to advance towards partition 956, fiber 977, which is affixed to the sleeve 980 by fiber lock 963, extends from the needle second end 944 as springs 982 begin to compress. The distance that the fiber 977 extends from the needle 940 is restricted by the sleeve flange 904 abutting against reversing microswitch 959.

Activation of switch 959 commands the control unit to discontinue injecting air into port 902 and begin pumping air into port 903. As such, the fiber distal end 978 is retracted back into the needle bore 946 and the needle 940 is retracted back into the needle collar bore 930.

In the device 910 of FIG. 13, the distance that needle 940 and fiber 977 advance substantially together is predetermined by adjustably positioning partition 956 within the housing 912 and tightening set screw 958. Further, the distance fiber 977 advances from the needle 940 is predetermined by positioning partition 992 within the housing 912 and tightening set screw 906.

Figure 14:
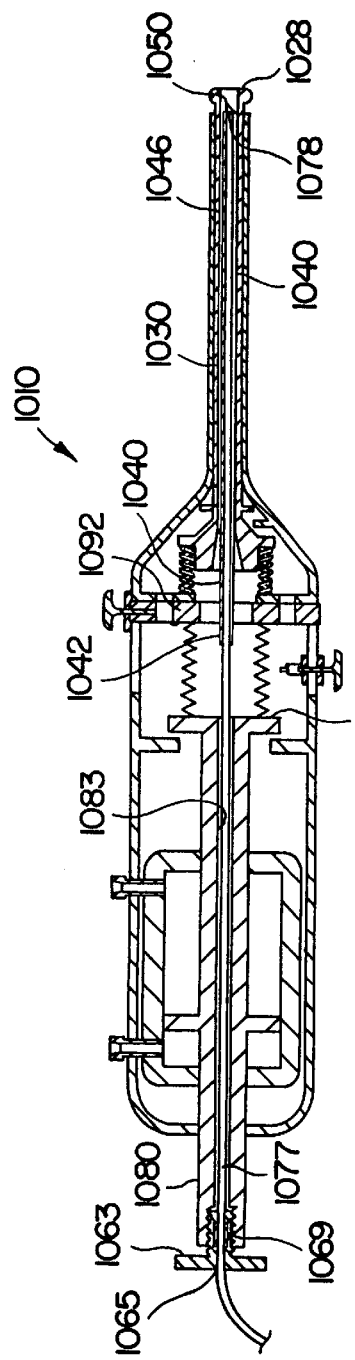
FIG. 14 is a cross-sectional side view of a further embodiment of the present invention with the needle crimped onto the fiber.

FIG. 14 illustrates another embodiment of the present invention which is similar to FIG. 11. However, instead of having a grip for detachably connecting the sleeve to the needle, the needle is crimped onto the fiber wherein any buffer coating may have earlier been removed therefrom. Correspondingly, where appropriate, the last two digits in the 1000 series of numerals depicted in FIG. 14 are connected to elements which have the same function and/or structure as those described with regard to FIGS. 1, 4, 5, 6, and 11.

In FIG. 14, device 1010 includes disposable needle 1040 and fiber 1077. The first end 1042 of the needle 1040 is crimped onto the fiber 1077 from which the fiber's buffer coating may have earlier been removed. Preferably, the distal end 1078 of the fiber is positioned within the needle bore 1046 and is proximate to needle point 1050.

The fiber 1077 is attached to the distal end of sleeve 1080 by fiber lock 1063. The fiber 1077 longitudinally extends through sleeve bore 1083. The fiber 1077 and attached needle 1040 also extend within the needle collar bore 1030 with, preferably, the needle point 1050 being positioned within the needle collar bore and proximate to the needle collar second end 1028.

The threaded fiber lock 1063 provides for selectably adjusting the distance between the needle point 1050 and the needle collar second end 1028. The fiber lock 1063 secures the position of the fiber 1077 and needle 1040, relative to sleeve 1080, by screwing the fiber lock into the bore 1083 of the sleeve 1080 such that compression fitting 1069 tightens around, and thus secures, the fiber.

The needle 1040 and fiber 1077 are installed within the device 1010 by loosing the compression fitting and inserting the needle pointed end 1050 into the fiber lock bore 1065. The needle 1040 is then advanced through the sleeve bore 1083 and into the needle collar bore 1030 by pushing fiber 1077 into the sleeve bore. Finally, the fiber lock 1063 is tightened onto the fiber 1077.

With the needle 1040 installed in the device 1010 as shown in FIG. 14, the needle first end 1042 extends out of the sleeve bore 1083. The needle 1040 is approximately 3 to 7 centimeters in length with a preferred length of 4 to 6 centimeters.

Axial movement of sleeve 1080 results in like moment of the fiber 1077 and needle 1040 since the fiber is attached to the sleeve and the needle is attached to the fiber. As such, the operation of device 1010 is similar to that described above for device 710 shown in FIG. 11.

FIGS. 15A and 15B illustrate other disposable fiber and needle configurations for use with the device of FIG. 14. FIG. 15A depicts a needle 1040a having a bore 1046a with an inner diameter of approximately 1.5 to 2.0 millimeters,. The needle 1040a is crimped onto a 500 to 1000 micron core fiber. In the event the buffer coating of the fiber is removed before crimping the needle to the fiber, the needle bore would be correspondingly smaller.

FIG. 15B shows a device consisting of a SPECTRA-PROBE needle which is a hollow lasing needle attached to the fiber as in U.S. Pat. No. 4,773,413, to Hussein et al., and incorporated herein by reference. (Trimedyne, Inc., Irving, Calif.). The SPECTRAPROBE needle 1040b has a bore 1046b with an inner diameter suitable for crimping the needle onto a 200–365 micron core diameter fiber or a bundle of 50–100 core fibers. The SPECTRAPROBE needle 1040b has an outer diameter of about 1.0 to 2.5 millimeters, preferably about 1.5 millimeters. Lens 1019 is fixed within bore 1046b and proximate to the distal end 1050 of SPECTRAPROBE needle 1040b. The lens 1019 diverges the laser energy emitted from the fiber distal end 1078 beam so that a channel larger than the diameter of the optical fiber 1077 is created.

Figure 16:
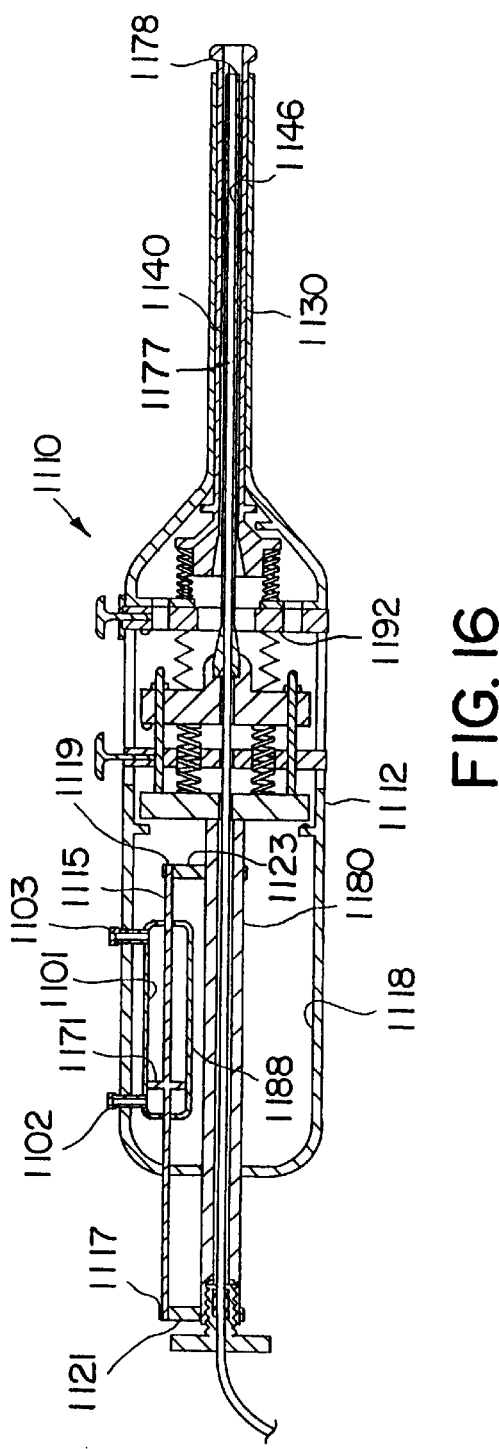
FIG. 16 is a cross-sectional side view of another device in accordance with the present invention wherein the device is actuated by using compressed air.

FIG. 16 depicts another embodiment of the present invention wherein the device is actuated by using compressed air. The device 1110 is similar to that shown in FIG. 13 except that the sleeve 1180 does not pass through cylinder chamber 1101 and the piston 1171 does not extend from the sleeve. Correspondingly, where appropriate, the last two digits in the 1100 series of numerals depicted in FIG. 16 are connected to elements which have the same function and/or structure as those described with regard to FIGS. 1, 4, 5, 6, and 13.

As illustrated by FIG. 16, cylinder 1188 is secured by conventional means to the housing 1112 within cavity 1118. Shaft 1115 slidably extends through the cylinder 1188 with piston 1171 radially outwardly extending from the shaft within the cylinder chamber 1101.

Preferably, shaft 1115 extends in spaced parallel relationship to sleeve 1180. The ends 1117,1119 of the shaft 1115 extend from the cylinder chamber and are attached, via arms 1121,1123, to the sleeve.

Ports 1102,1103 extend from the device housing 1112 and provide for a fluid medium, preferably air, to ingress and egress from the chamber 1101. The injection of air within port 1102 pushes piston 1171, and thus interconnected sleeve 1180, towards partition 1192. This results in the needle 1140 and fiber 1177 advancing together into the epicardium of the heart and then the fiber, alone, advancing through the endocardium.

Conversely, the injection of air into port 1103 pushes piston 1171, and thus sleeve 1180, away from partition 1192. As such, the fiber distal end 1178 is retracted back into the needle bore 1146 and the needle 1140 is retracted back into the needle collar bore 1130.

Figure 17:
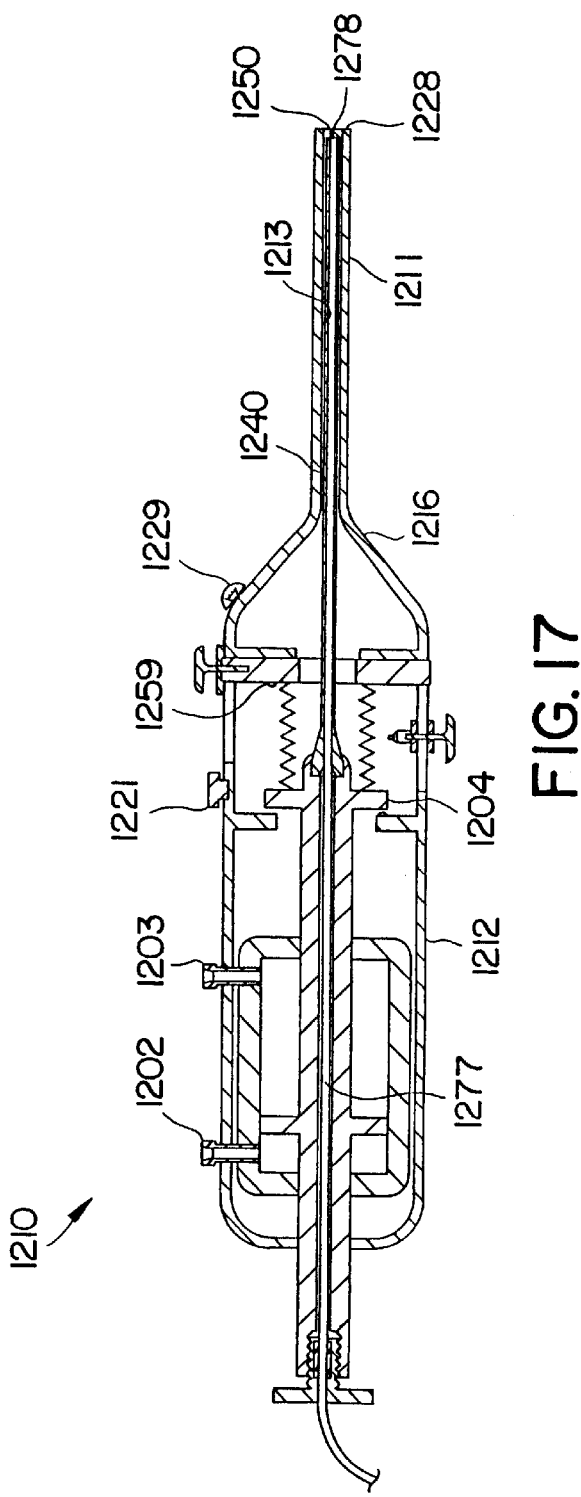
FIG. 17 is a cross-sectional side view of yet another embodiment of the present invention.

FIG. 17 provides a cross-sectional side view of yet another embodiment of the present invention having an activating button and arming light emitting diode (LED). The device 1210 of FIG. 17 is similar to that depicted in FIG. 11 except that needle collar 725 has been eliminated. Correspondingly, where appropriate, the last two digits in the 1200 series of numerals depicted in FIG. 17 are connected to elements which have the same function and/or structure as those described with regard to FIGS. 1, 4, 5, 6, and 11.

In FIG. 17, shaft 1211 extends from the second end 1216 of the housing 1212. The needle 1240 extends within an open bore 1213 passing through the shaft 1211. Preferably, the needle 1240 is positioned within bore 1213 with the needle point 1250 located proximate to the distal end 1228 of the shaft 1211.

Mounted to the housing are activating button 1221 and indicator LED 1229. The activating button 1221 is connected to the control unit by conventional means to command the control unit to advance and retract the needle 1240 by injecting air into ports 1202 and 1203, respectively. Moreover, the indicator LED is operably connected to the control unit to indicate when the laser unit is ready to transmit laser energy via fiber 1277.

In operation, the shaft distal end 1228 is held against the heart's surface. If indictor LED 1229 is illuminated to indicate that laser energy is available for making a channel in tissue, activating button 1221 is depressed.

The control unit injections air into port 1202 to advance the needle point 1250 from the bore 1213 of shaft 1211. The needle 1240 is fully extended when sleeve flange 1204 abuts against switch 1259 which indicates that the control unit is to retract the needle. Correspondingly, the control unit stops injecting air into port 1202 and begins injecting air into port 1203 which results in the needle being retracted back into bore 1213.

Preferably, during the advancement and retraction of the needle 1240 from bore 1213, laser energy is transmitted into fiber 1277 and emitted from the fiber distal end 1278 in the same manner as that described for the embodiment shown in FIG. 11.

Figure 18:
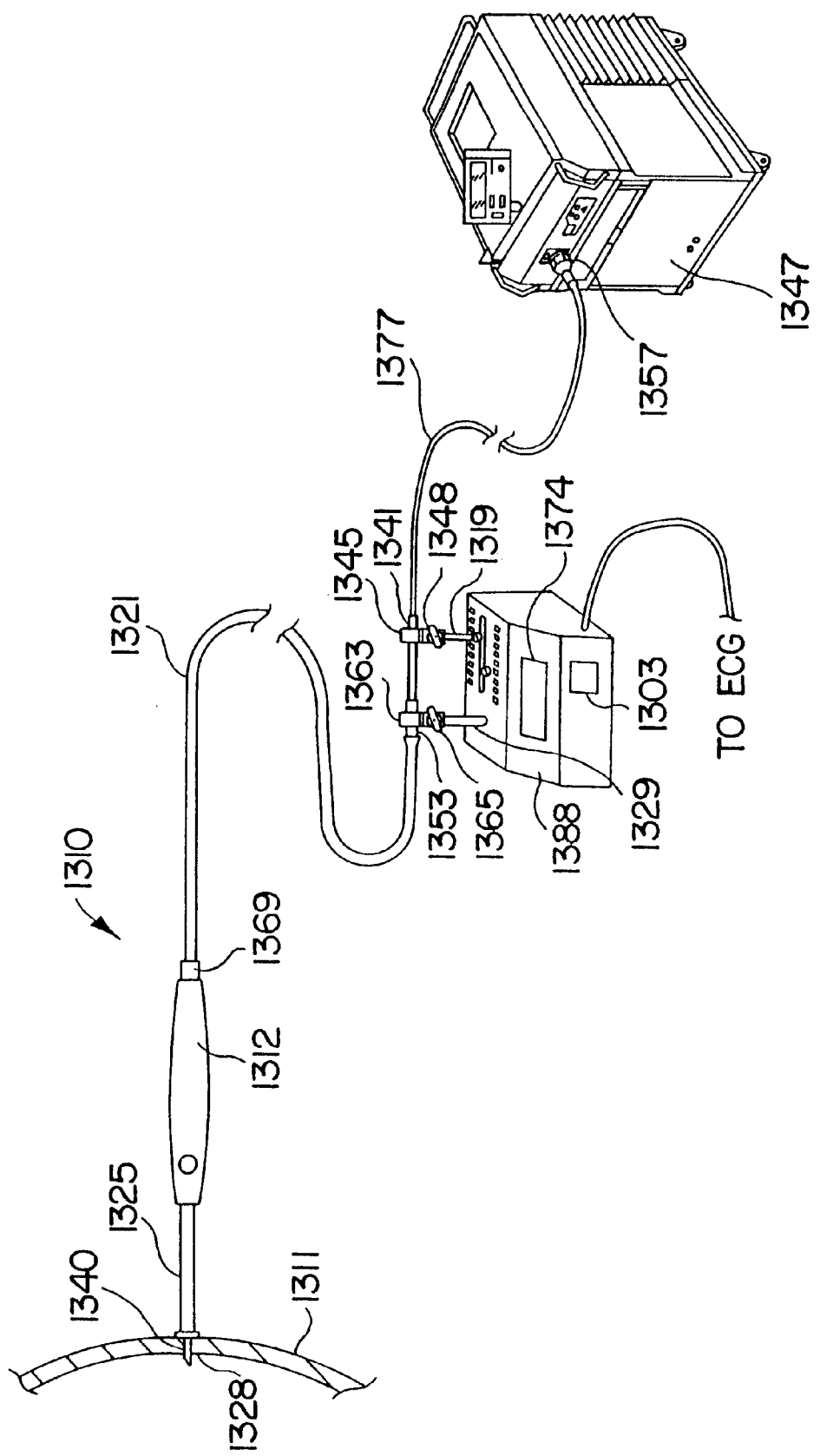
FIG. 18 is a perspective view of another embodiment of the present invention having an external actuator for advancing and withdrawing the fiber and needle from a handpiece.

FIG. 18 provides a perspective view of a preferred embodiment of the present invention wherein an external actuator is used for advancing and withdrawing the optical fiber and needle from a handpiece. The operation of the device shown in FIG. 18 is similar to the embodiments described above. Correspondingly, where appropriate, the last two digits in the 1300 series of numerals depicted in FIG. 18 are connected to elements which have the same function and/or structure as those described with regard to FIGS. 1, 4, 5, 6, and 11.

The device 1310 of FIG. 18 is operatively connected to external actuator 1388 which minimizes both the size and weight of the handpiece or housing 1312. Further, the embodiment of FIG. 18 reduces the number of leads that must be connected to the handpiece 1312 such as air lines and electrical wires for advancing the needle and receiving feedback regarding the needle's position as it is being advanced.

The external actuator 1388 is operably connected to handpiece 1312, a laser energy source 1347, and a conventional ECG (not shown). The laser 1347 is connected to fiber 1377 by conventional fiber optical connector 1357. The laser 1347 receives position signals and command signals from the handpiece 1312 and actuator 1388. When enabled by activation of a footswitch or other means, a preselected amount of laser energy is transmitted into fiber 1377 in response to the position signals. The laser energy is transmitted, via fiber 1377, to the handpiece 1312.

Besides being connected to the laser 1347, the fiber 1377 is also connected to the actuator 1388. The fiber 1377 is attached to drive arm 1319 of actuator 1388 and extends through a flexible cannula 1321 into the handpiece 1312. The fiber 1377 is allowed to slide within the cannula 1321 with one end of the cannula being attached to a fixed arm 1329 of the actuator 1388 and the other end of the cannula being attached to the handpiece 1312.

Figure 19:
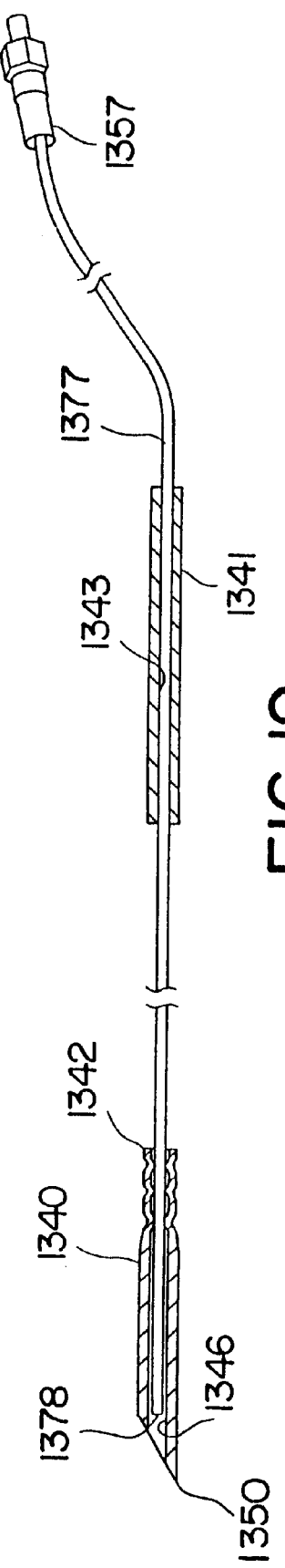
FIG. 19 is a perspective partially cross-sectional view of the needle and fiber of FIG. 18 with a support tube attached to the fiber.

As shown in FIG. 19, needle 1340 is attached proximate to the distal end of fiber 1377. The needle 1340 has a length of about 1 to 10 centimeters, preferably about 4 to 7 centimeters. The first end 1342 of the needle 1340 is crimped onto the fiber 1377, from which the fiber's buffer coating may have earlier been removed. Further, the distal end 1378 of the fiber is preferably positioned within the needle bore 1346 and is proximate to needle point 1350.

A support tube 1341 is also attached to the fiber 1377 for preventing the core of the fiber from being damaged by the force exerted by advancing the drive arm 1319 of actuator 1388. The support tube 1341 is preferably made of metal or a metal alloy and has a longitudinal open bore 1343 for receiving the fiber 1377 which passes through the bore. The fiber 1377 is secured to the tube 1341 by glue or the like.

Returning to FIG. 18, the outer surface of support tube 1341 is removably grasped by clamp 1345 of drive arm 1319. The clamp 1345 releases and secures the support tube 1341 by loosing and tightening, respectively, clamp adjustment handscrew 1348.

Figure 20:
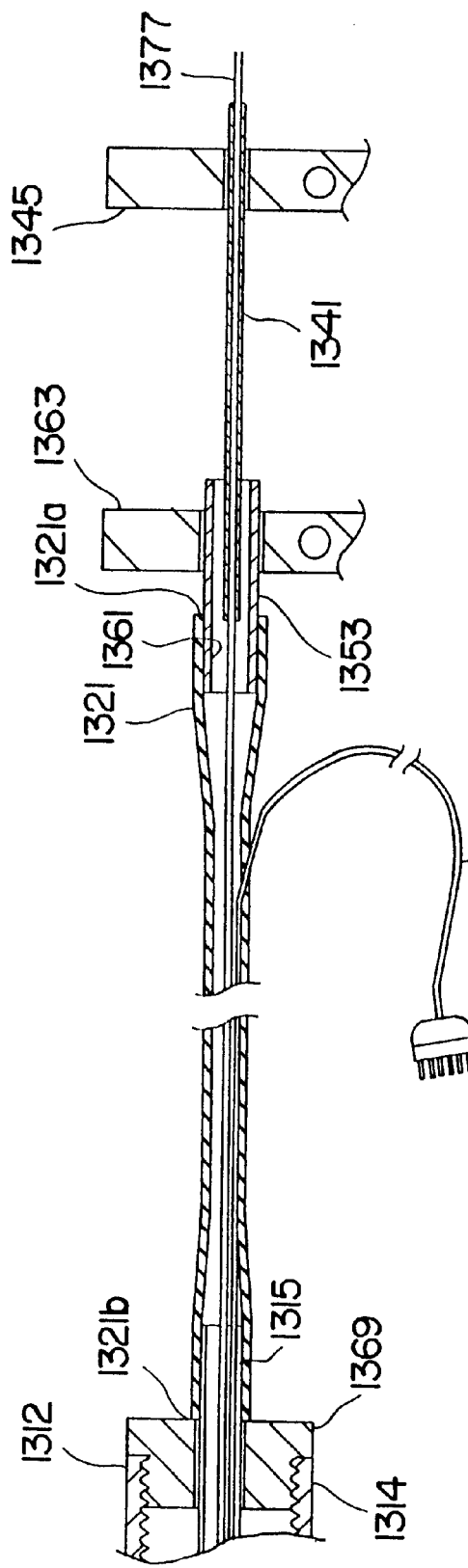
FIG. 20 is a cross-sectional view of the fiber of FIG. 18 passing through both the support tube and a bushing, and then extending into the handpiece.

FIG. 20 depicts the support tube 1341 and attached fiber 1377 passing through a bushing 1353 removably mounted onto the fixed arm 1329 of the actuator 1388. The bushing 1353 may be made of metal or plastic and has a longitudinal open bore 1361 for slidably receiving support tube 1341 and fiber 1377. The inner diameter of the bushing bore 1353 is greater than the outer diameter of the support tube 1341 in order to allow the support tube to freely slide within the bushing 1353.

The bushing 1353 is removably mounted to clamp 1363 of fixed arm 1329. The outer surface of the bushing 1353 is removably grasped by the clamp 1363. The clamp 1363 either releases or securely holds the tube by loosing or tightening, respectively, clamp adjustment handscrew 1365.

One terminal end 1321a of the cannula 1321 is attached to the bushing 1352 by partially inserting the bushing into the cannula 1321. Glue or the like may also be used in securing the cannula 1321 to the bushing 1352.

The other terminal end 1321b of the cannula 1321 is connected to a nipple 1315 extending from plug 1369 of handpiece 1312. The cannula 1321 is fitted over the outer surface of the nipple 1315 and may be secured to the nipple by glue or the like.

Figure 21:
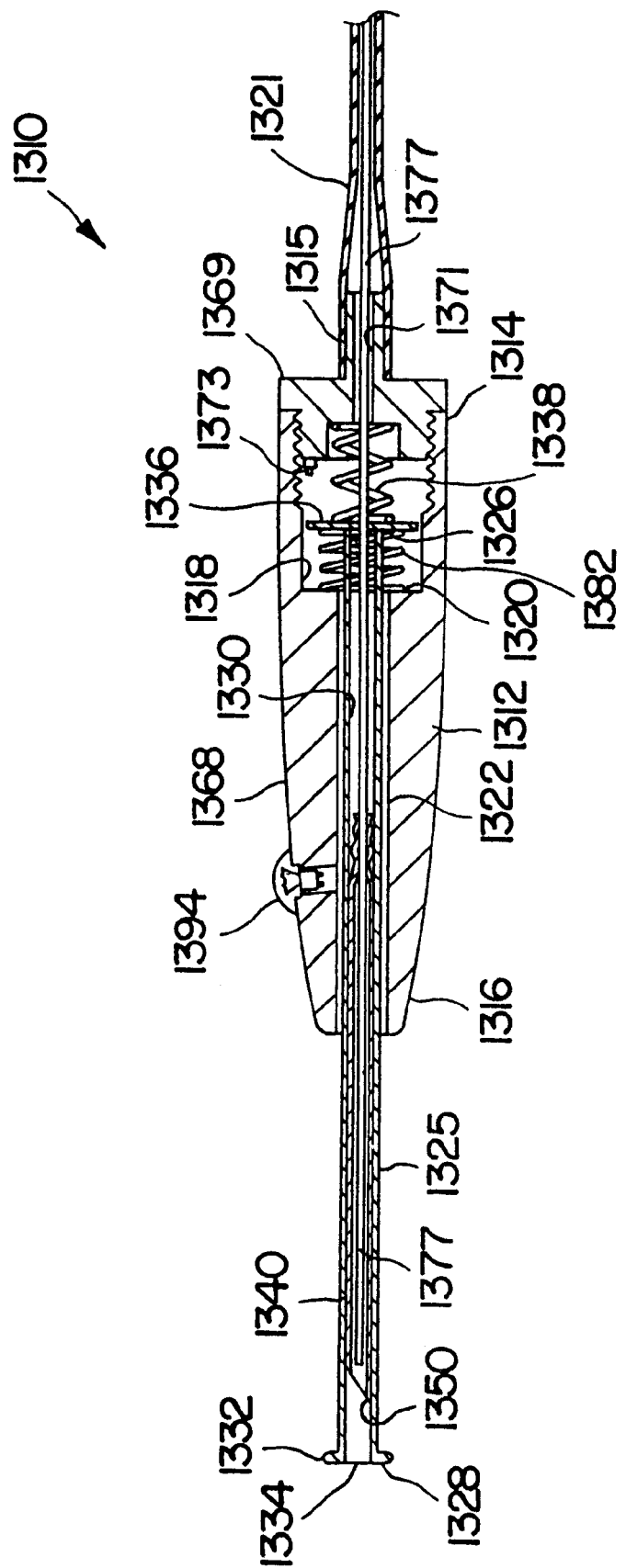
FIG. 21 is a partial cross-sectional view of the handpiece of FIG. 18.

FIG. 21 provides a partial cross-sectional view of the handpiece 1310. The handpiece 1310 includes a generally cylindrical housing 1312 having a first end 1314 and a tapered second end 1316 with an elongated cavity 1318 extending therebetween.

Extending within the housing cavity 1318 is a shoulder 1320. The shoulder 1320 is ring shaped and results in the housing cavity 1318 having a cylindrical longitudinal portion or passage 1322 that is in communication with the outside 1368 of the housing 1312 at the first end 1316.

Slidably mounted within the housing cavity 1318 and extending from the first end 1316 of the handpiece 1310 is a hollow needle collar or guide 1325. The needle collar 1325 is generally cylindrical in shape with an inner end 1326, an outer end 1328, and an open bore 1330 extending therebetween.

The inner end 1326 of the needle collar 1325 extends past shoulder 1320 and has a radially outwardly extending retaining ring 1336 with a larger outer diameter than the inner diameter of cavity passage 1322. Likewise, the outer end 1328 of the needle collar 1325 which protrudes from passage 1322 has a rounded flange 1332 extending around its periphery. The rounded flange 1332 results in the outer end 1328 of the needle collar 1325 having a flat disk shaped surface with the aperture 1334 to bore 1330 being located in the center.

Located between retaining ring 1336 and shoulder 1320 is coiled spring 1382 which wraps around the outer surface of the needle collar 1325. The coiled spring 1382 retractably biases the collar 1325 towards the first end 1314 of the housing 1312.

Threading mounted onto the first end 1314 of the housing 1312 is plug 1369 having an open bore 1371 in communication with the housing cavity 1318 and extending through nipple 1315. Extending through plug bore 1371 and into the needle collar bore 1330 is fiber 1377.

Further, mounted onto the plug 1369 is an electrical switch 1373 which faces towards retaining ring 1336. The switch 1373 provides a means for detecting when the needle collar 1325 has been pushed a fixed distance within the housing cavity 1318. Correspondingly, the switch 1373 is activated only when the retaining ring 1336 of the needle collar 1325 abuts against the switch.

Resiliently biased against retaining ring 1336 and plug 1369 is coiled spring 1338 which forward biases the collar 1325 away from the first end 1314 of the housing 1312.

Attached to the housing 1312 is LED 1394 for indicating that the device 1310 is either ready to, or has completed, making a channel within tissue. The LED 1394 is operably connected to the control unit 1347 by conventional means such as wire leads within wire harness 1395.

Figure 22:
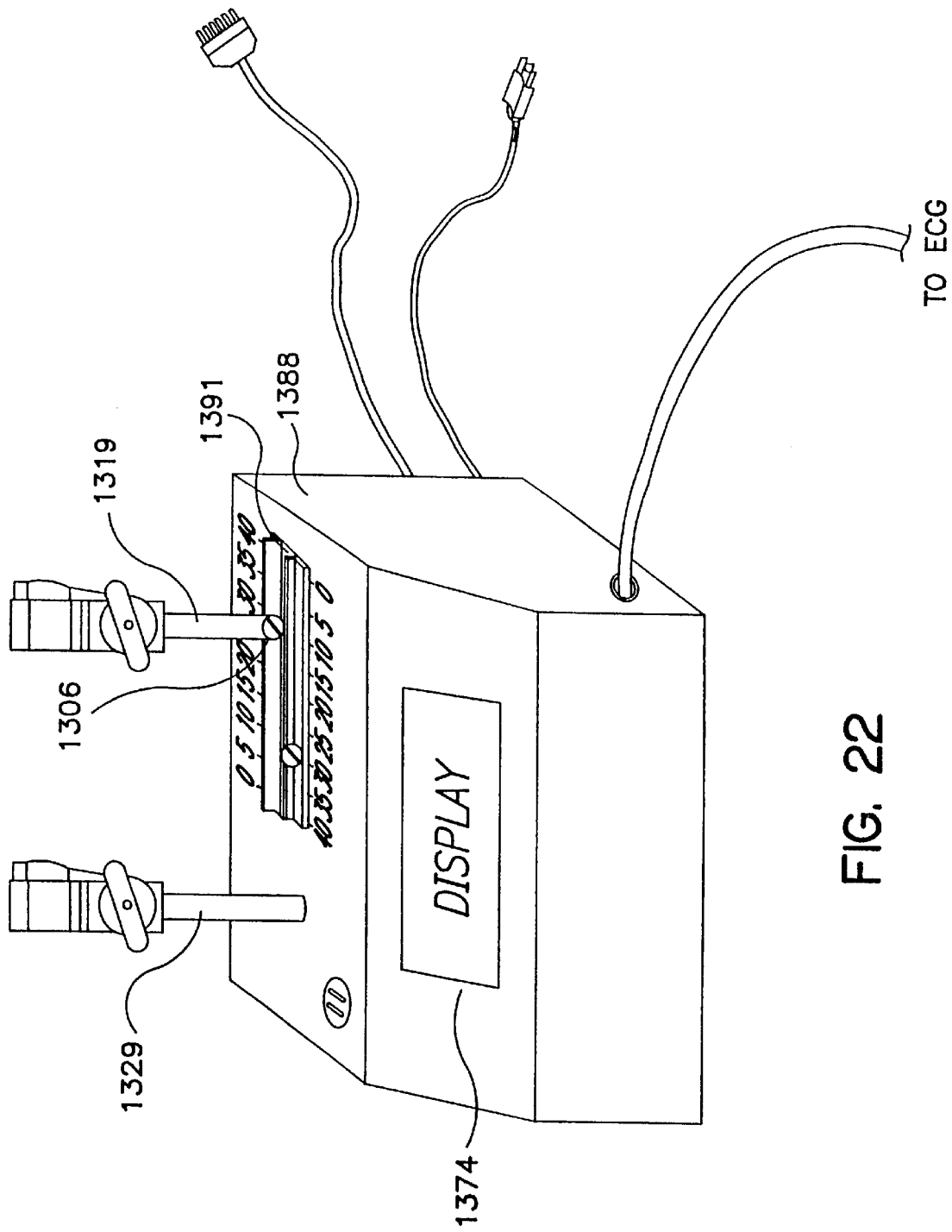
FIG. 22 is a perspective view of the external actuator depicted in FIG. 18.
Figure 24:
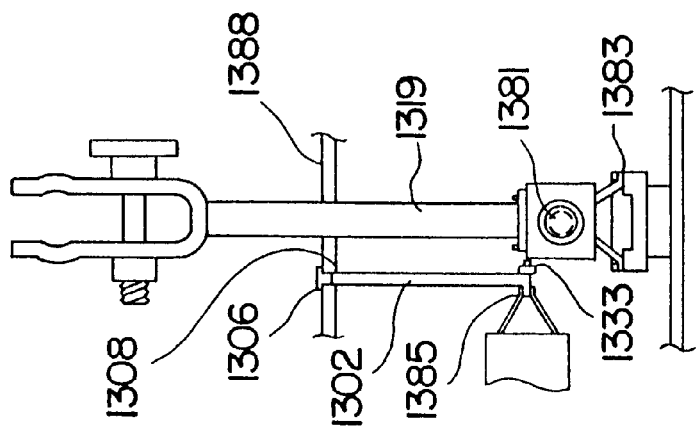
FIG. 24 is an end view of the external actuator along line 24—24 of FIG. 23.
Figure 23:
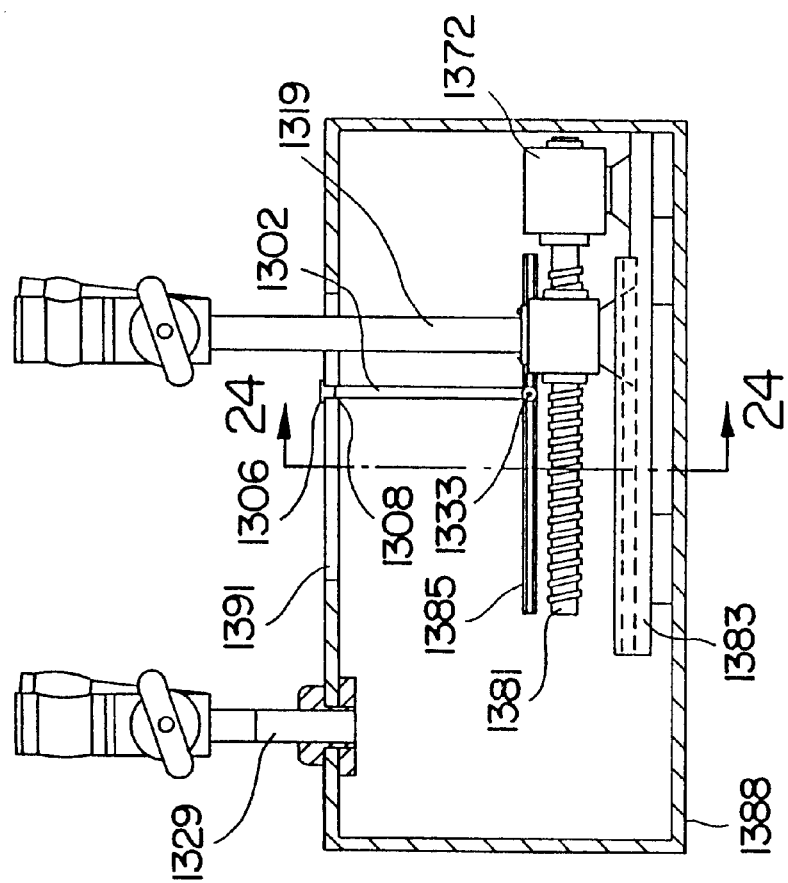
FIG. 23 is a fragmentary partial cross-sectional side view of the external actuator of FIG. 22.

FIGS. 22–24 depict the external actuator 1388 for advancing and withdrawing the optical fiber 1377 and needle 1340 from the handpiece 1310. The actuator 1388 includes a stepper motor 1372 and a conventional active touch-screen display 1374. The stepper motor 1372 operates to advance and withdraw the optical fiber 1377 and needle 1340 by moving drive arm 1319 towards and away from fixed arm 1329.

As seen in FIG. 23, stepper motor 1372 is mounted to the actuator housing and operates to bi-directional rotate shaft 1381 which is threadingly engaged by drive arm 1319. Also mounted to the actuator housing and in spaced parallel relationship to shaft 1381 is track 1383 for sliding engaging drive arm 1319 between the stepper motor 1372 and fixed arm 1329.

In operation, longitudinal axial rotation of the shaft 1381 by the stepper motor 1372 in the clockwise direction, for example, results in the drive arm 1319 advancing towards the fixed arm 1329. Conversely, rotation in the counterclockwise direction moves the drive arm 1319 away from the fixed arm 1329.

Also mounted to the housing of the external actuator is an elongated track 1385 for slidingly adjusting the position of sensor 1333. The track 1385 is generally in spaced parallel relationship to the stepper motor shaft 1381. The sensor 1333 can be moved along track 1385 by attached post 1302 which extends into a elongated channel 1391 between arms 1319 and 1329.

Threadably attached to the distal end 1308 of post 1302 is a set screw 1307 for adjustable fixing the position of sensor 1333 along track 1385. The set screw 1307 abuts against the outside of the actuator housing and is adjustably secured to the housing by tightening the set screw. Correspondingly, positioning of the set screw 1308 results in like placement of the sensor 1333 along track 1385.

The sensor 1333 is activated, preferably, when it comes in contact with, or is brushed by, drive arm 1319. As such, the sensor 1333 detects when the drive arm 1319 is within a predetermined distance from the fixed arm 1329 which corresponds to the distance that the needle 1340 is advanced, or retracted, from the second end 1328 of the needle collar 1325.

Figure 25:
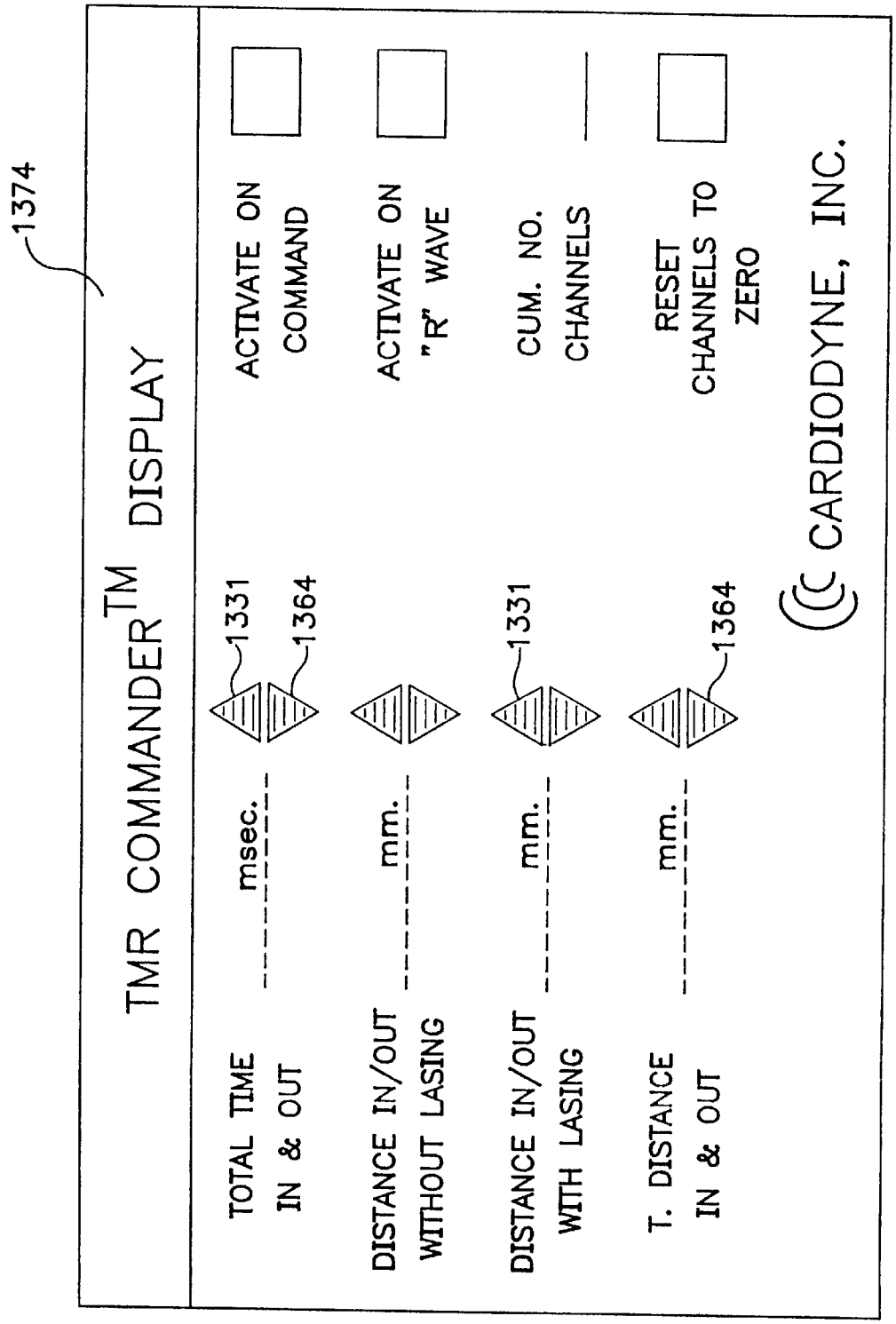
FIG. 25 is a touch-screen display provided by the external actuator of FIG. 22.

FIG. 25, depicts a preferred embodiment of the display 1374 provided by the external actuator 1388. The display 1374 provides for selection and activation of various functions to be performed during a TMR procedure. The display 1374 is stimulated by conventional means such as the touch of a finger.

The display 1374 includes options such as a "ACTIVATE ON COMMAND" touch area for activating the device 1310 to form a channel by depressing a button mounted on the handpiece or the like. The display 1374 also includes an "ACTIVATE ON "R" WAVE" touch area to command the device 1310 to form a channel when the next recognizable "r" wave is determined. Further, the display 1374 includes a "CUMULATIVE NUMBER OF CHANNELS" area for displaying how may channels have be formed by the device 1310. The count shown on the "CUMULATIVE NUMBER OF CHANNELS" area can be reset to zero by touching the "RESET CHANNELS TO ZERO" touch area.

Other operational settings such as the time and distance that the needle 1340 is to advance and retract from the handpiece 1312 are provided by the display 1374. These settings are selected by up touch area arrows 1331 and down touch area arrows 1364 provided on the display.

Referring back to FIGS. 18 and 26, the laser 1347 is enabled by depressing a footswitch or the like. The laser 1347 initially provides laser energy which is diverted into a heat sink by a mirror or shutter as explained above. The device 1310 is then operated by pressing the second end 1328 of the needle collar 1325 against heart 1311 until retaining ring 1336 abuts against switch 1373. Activation of switch 1373 results in the illumination of LED 1394 to indicate that the device 1310 is armed and is awaiting the next recognizable "r" wave of the patent's ECG.

Within the external actuator 1388 is a controller 1303 for determining when to form the channel in heart 1311. The controller 1303 makes its determination by interposing an appropriate delay time from the next recognizable "r" wave of the patient's ECG, while taking care to avoid activation in the event any unusual variation in heart rhythm.

When the controller 1303 determines that a channel is to be made, the controller operates stepper motor 1372 to advance movable arm 1319 towards fixed arm 1329. As the arms 1319,1329 are moved towards each other, support tube 1341 is pushed further within bushing 1353 which advances needle 1340 from the second end 1328 of the needle collar 1325 and into heart 1311. As the fiber 1377 and attached needle 1340 are being advanced, movable arm 1319 actives switch 1333 which results in laser energy being emitted, via fiber 1377, from the fiber distal end 1378. The laser energy is, preferably, transmitted into the fiber by retracting a shutter or mirror within the laser unit 1347 as explained, in detail, above.

The microcontroller 1303 continues to advance the needle 1340 until it is advanced the preselected distance entered by the surgeon using display 1374 as depicted by FIG. 26. Thereafter, the microcontroller 1303 reverses the rotational direction of the stepper motor to retract the needle 1340 back into needle collar 1325.

As the needle 1340 is being retracted, movable arm 1319 again activates switch 1333 which stops the transmission of laser into fiber 1377 by deflecting the laser energy provided by the laser unit 1347 into a beam dump as explained, in detail, above.

The microcontroller 1303 continues to retract the needle 1340 until the needle point 1350 is positioned back into the needle collar bore 1330. The LED 1394 is then turned off by microcontroller 1303 to indicated that the channel making process has been completed.

The surgeon may then remove his foot from the laser's footswitch and reposition the handpiece 1312 to repeat the process of making a channel in the heart 1311 or he may continue to depress the footswitch throughout the making of any number of channels.

FIG. 27 depicts a cross-sectional view of another handpiece in accordance with the present invention. The handpiece 1412 is similar to that shown in FIG. 21 except that the needle collar 1425 is securely mounted to the handpiece and an activating button 1467 is provided. Correspondingly, where appropriate, the last two digits in the 1400 series of numerals depicted in FIG. 27 are connected to elements which have the same function and/or structure as those described with regard to FIGS. 18–26.

In FIG. 27, needle collar 1425 is secured to plug 1369 and extends from the second end 1416 of the handpiece 1412. Attached to the portion 1437 of the needle collar 1425 that extends from the handpiece second end 1416 is cannula 1421.

The fiber 1477 within the cannula 1421 extends into the needle collar bore 1430. The pointed end 1450 of the needle 1440 attached to the fiber 1477 is positioned proximate to the needle collar second end 1428.

Activating button 1467 is mounted on the outside of the handpiece 1412 and is operably connected to the control unit. The button 1447 is depressed by a surgeon when the second end of the needle collar 1428 is abutted against the heart. Depressing the button 1640 commands the device to being forming a channel in the heart as described above with regard to FIGS. 18–26.

Referring to FIGS. 18 and 27, by adjusting the position of fiber 1477 within clamp 1345 of activator arm 1319, the distal end 1450 of needle 1440 may be extended 1 to 6 millimeters, preferably about 3 to 4 millimeters, distally from flange 1428 of needle collar 1425. In this embodiment, when device 1412 is pressed against the heart, needle 1440 penetrates into the epicardium. When button 1467 is depressed on the next recognizable "r" wave, the needle 1440 and fiber 1477, with laser transmission, advance through the endocardium into the heart chamber and retract to their original position. Device 1412 and needle 1440 are then manually withdrawn from the heart.

FIG. 28 shows an alternate embodiment of the handpiece shown in FIG. 27 except that the needle collar is detachably secured to the handpiece and is curved at an angle of approximately thirty (30) degrees.

In FIG. 28, a threaded collar fitting 1570 is attached to the first end 1514 of the handpiece 1512. The needle collar 1525 longitudinally extends through an open bore 1575 in fitting 1570 and into housing cavity 1518. Adhesive 1576 is used to secure the needle collar to the fitting 1570. Further, the portion of the needle collar 1525 which extends from the handpiece 1512 is bent at an angle of approximately thirty degrees (30°).

In this embodiment, needle 1540 is 0.5 to 2.0 centimeters in length, preferably about 0.8 to 1.5 centimeters in length. Tubing 1584 surrounds the fiber 1577 and is attached proximate to needle 1540 to avoid the proximal end of needle 1540 hanging up on flange 1528 of needle collar 1525 when being retracted thereinto. Preferably, the tubing 1584 is made of plastic and has the same outside diameter as that of the needle 1540. The tubing 1584 is attached to the fiber 1577 by adhesive.

Tubing 1584 is about 2 to 10 centimeters in length, and preferably is 6 centimeters in length, such that the tubing is longer than the stroke length of the external actuator.

FIG. 29 illustrates another handpiece 1612 which is similar to that shown in FIG. 28 except that the portion of the needle collar 1625 which extends from the handpiece is bent at an angle of approximately ninety degrees (90°). Alternate shapes of needle collar 1625 may range from 20° to 180°.

In the device 1310 previously disclosed and illustrated by FIGS. 18–26, considerable recoil was encountered when the needle 1340 penetrated the epicardium, which is a tough, very dense, outer layer of the heart muscle. This recoil can be reduced by increasing the rate at which needle 1340 penetrates the epicardium, ramping up to the speed at which the needle 1340 penetrates the endocardium. The recoil effect can also be reduced, as described above, by allowing the needle 1340 to extend 3 to 6 millimeters from the second end 1328 of the needle collar 1325. When the second end 1328 of needle collar 1325 is manually pressed against the heart, the needle passes into or through the epicardium. When the external actuator 1388 is activated, significantly less recoil results as the needle 1340 traverses the remainder of the epicardium and the endocardium.

However, in order to prevent scratching of the heart or other tissue by the exposed needle when moving the device around the side or posterior surface of the heart, the needle may be temporarily retracted within the tube and extended when the device has been re-positioned.

Extending the needle from the tube also allows the needle to cool more effectively in the air, after lasing, and avoids heating the second end 1328 of the needle collar 1325 by not enclosing the hot needle therewithin.

Another benefit of extending the needle 1340 3 to 6 millimeters from the second end 1328 of the needle collar 1325 is that additional lasing time is obtained, allowing for more energy pulses to be emitted and a more uniform, larger diameter channel to be created. For example, if the heart wall is 15 millimeters thick, in the earlier described procedure, the needle would travel a total of 18 millimeters (3 millimeters into the heart chamber) and 18 millimeters back. Of this distance, for example, 4 millimeters in and 4 millimeters out of the epicardium would be without lasing. If the entire insertion and withdrawal is done in 0.4 seconds of the 0.6 second period of diastole, assuming a heart rate of 60, the rate of speed would be 36 millimeters in 0.4 seconds or 90 millimeters/second. Lasing would occur during 28 millimeters of the total 36 millimeters distance for 0.313 seconds (0.78 of 0.04 seconds). At a pulse repetition rate of 30 Hertz (2 joules per pulse), an average of 9.39 pulses would be emitted.

However, if the needle extends 4 millimeters distally from the needle collar, the total distance traveled, in and out, would be 28 millimeters (11 millimeters+3 millimeters in and 11 millimeters+3 millimeters out). Lasing can occur during the entire 0.4 second period. At the same pulse repetition rate of 30 Hertz, 12 pulses of energy would be emitted.

Figure 30:
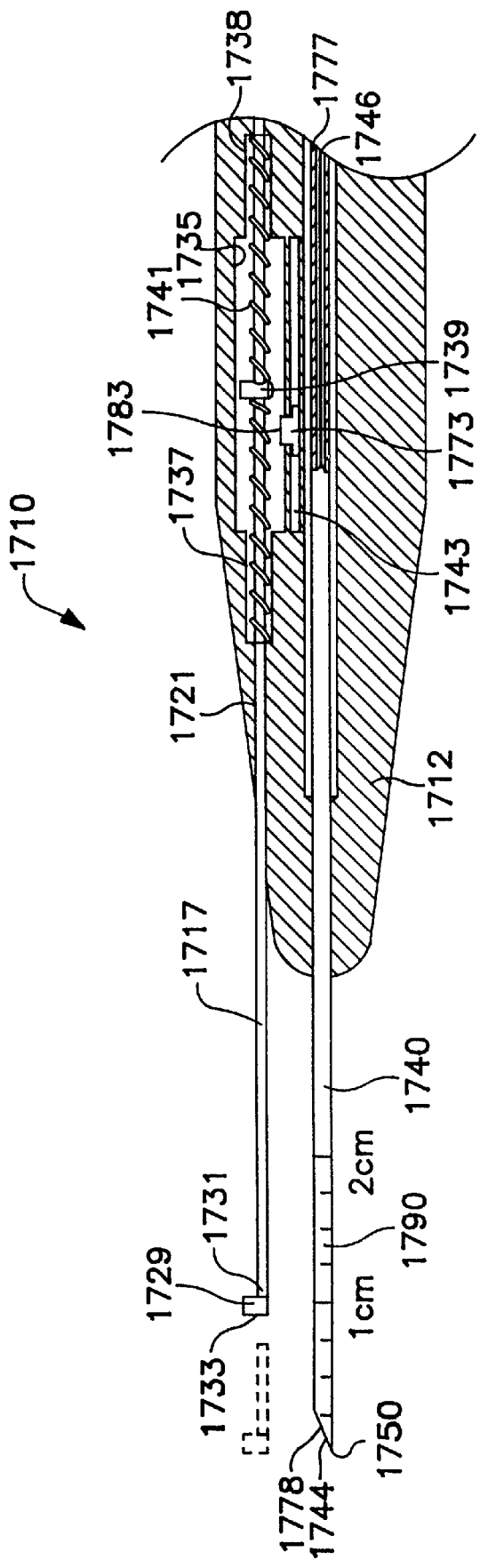
FIG. 30 is a partial cross-sectional view of another embodiment of a device in accordance with the present invention.

FIG. 30 illustrates yet another embodiment of the present invention. Where appropriate, the last two digits in the 1700 series of numerals depicted in FIG. 30 are connected to elements which have the same function and/or structure as those described with regard to FIGS. 1, 4, 5, 6, and 11. Similarly, the last two digits in the 1800 series and 1900. In this particular embodiment, actuator rod 1717 is employed to actuate switch 1773 located within housing 1712 of device 1710. The switch 1773 controls the transmission of the laser energy through the optical fiber 1777.

Device 1710 includes, in addition to housing 1712, a hollow needle 1740 having a bore 1746, and optical fiber 1777 received within bore 1746. The optical fiber-and-needle configuration is similar to the embodiments described hereinabove. However, in lieu of a hollow guide coaxial with the needle, as in the previous embodiments, device 1710 includes an actuator rod 1717 slidably received in an actuator rod channel 1721 defined by the housing 1712. Actuator rod 1717 cooperates with switch 1773 to control the transmission of laser energy, as do the hollow needle guides and the switches of the other embodiments described hereinabove.

In this embodiment, hollow needle 1740 and optical fiber 1777 contained therein are manually advanced into the tissue by moving housing 1712 forward the desired distance. Markings 1790 out the outer surface of the needle proximate to the distal end 1744 may assist the operator by indicating the distance the device has penetrated into the tissue.

Actuator rod 1717 protrudes from the housing 1712 and preferably includes a pad 1729 on its protruding distal end 1731 The pad 1729 includes distal surface 1733 that is substantially aligned with the point 1750 at the distal end 1744 of the needle 1740 when device 1710 is not in use. In use, the distal surface 1733 of the pad 1729 is urged against the epicardium of the heart as the needle 1740 is about to penetrate the epicardium. As the housing 1712 is advanced toward the heart so that the needle 1740 penetrates the epicardium, the actuator rod 1717 is moved back into the channel 1721 defined by the housing 1712.

The housing 1712 further defines an elongated chamber 1735 in communication with channel 1721. Chamber 1735 defines counterbores 1737 and 1738 that are coaxial with and extend longitudinally from each end of chamber 1735. Counterbores 1737 and 1738 also communicate with channel 1721. Actuator rod 1717 is received in the channel 1721 and extends through the chamber 1335 including the opposed counterbores 1737 and 1738. A ridge 1739 is located on the rod 1717 within the chamber 1735. The ridge 1739 extends radially from the rod 1717. A coil spring 1714 is preferably included coaxially on the rod 1717 within the chamber 1735 to bias the rod 1717 against the epicardium of the heart when in use and to hold the rod 1717 in an axial position when not in use such that pad 1729 is substantially aligned with the distal end 1744 of the needle 1740. Two springs 1741 are situated on either side of the ridge 1739 and extend into the counterbores 1737 and 1738.

Ridge 1739 is operably associated for with interaction switch 1773 that is located within a slot 1743. Slot 1743 is defined within the housing 1712 and is located alongside chamber 1735. Slot 1743 communicates with chamber 1735 such that a projection 1783 extends into chamber 1735. Projection 1783 is operably associated with ridge 1739 such that the ridge 1739 operates switch 1773 by moving the projection 1783 while rod 1717 moves the ridge 1739 past the switch 1773. Alternately, the ridge 1739 can extend from the chamber 1735 into the slot 1743 so as to contact the projection 1783, thereby operating the switch 1773.

Switch 1773 is movable longitudinally within slot 1743. The switch 1773 can be located at any location within the slot 1743 so that the ridge 1739 actuates switch 1773 when the needle 1740 reaches a preselected depth within the heart tissue. Switch 1773 is moved manually along slot 1743 to the desired position and may be temporarily fastened in place by a bolt or screw (not shown).

The depth at which the laser energy is triggered by the switch 1773 is controllable by selecting the longitudinal location of the switch 1773 within the slot 1743. For example, if the switch 1773 is located further away from the distal end 1744 of the needle 1740, the needle 1740 must penetrate deeper into the heart tissue in order to move the actuator rod 1717 back far enough so that the ridge 1739 contacts the switch 1773.

The switch 1773 preferably controls the transmission of the laser energy through the optical fiber 1777. The control of the laser energy transmission can by accomplished, for example, with any of the embodiments previously described. Preferably, the operator of the device 1710 energizes a laser energy source, with a foot pedal or the like, for example that point laser energy is transmitted into a shutter that is controlled by the switch 1773 in a manner, similar to the embodiment of FIG. 12. When the needle reaches a desired preselected depth into the heart tissue, the ridge 1739 contacts the switch 1773 which opens the shutter to allow the laser energy to be transmitted through the optical fiber 1777 and emitted from the distal end 1778 of the fiber 1777.

When the needle 1740 is removed from the tissue, the spring 1741 urges the rod 1717 back, out of the housing 1712, and moves the ridge 1779 past the switch 1773 in the opposite direction to close the shutter and thus end the transmission of laser energy through the optical fiber 1777. Switch 1773 is preferably a miniature toggle switch that causes the shutter to open when projection 1783 is moved in one direction, and causes the shutter to close when the projection 1783 is moved back in the opposite direction. In this manner, laser energy can be applied to form a channel during insertion as well as withdrawal of the needle 1740. Alternatively, the laser source can include a control mechanism that fires the laser for a preselected period of time once switch 1773 is activated. This alternate approach allows the channel to be formed only for a preselected time period, such as when the optical fiber 1777 is moving into the endocardium, for example.

Figure 31:
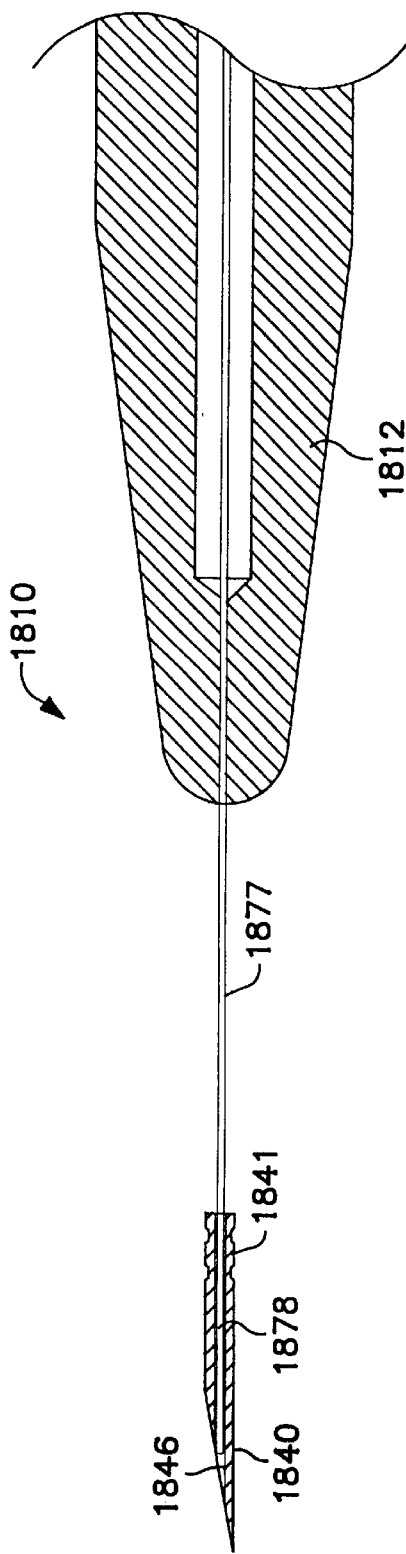
FIG. 31 is a cross-sectional view of another handpiece in accordance with the present invention wherein the optical fiber is disposed within the needle.
Figure 32:
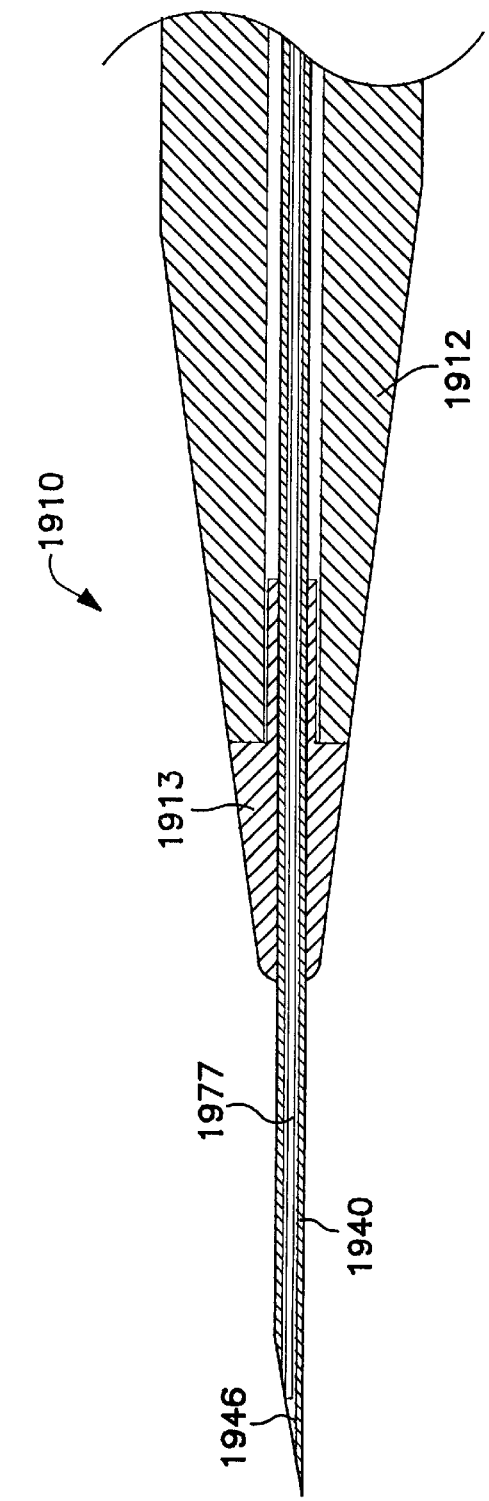
FIG. 32 is a cross-sectional view of yet another handpiece in accordance with the present invention wherein the needle is secured to the handpiece housing.

FIGS. 31 and 32 illustrate further embodiments of the needle and the tapered end of the housing from which the needle protrudes. In these particular embodiments an actuator, such as actuator rod 1717 shown in FIG. 30, can be omitted. An appropriate laser source, operably associated with the optical fiber surrounded at least in part by a hollow needle, can be energized by a conventional switch such as a foot pedal or a button mounted to the device in any convenient manner. In these embodiments, the device is advanced into tissue manually, instead of by a mechanism as described earlier.

Referring specifically to FIG. 31, optical fiber 1877 is mounted in handle housing 1812. Fiber 1877 is received within bore 1846 of hollow needle segment 1840 which is carried in this instance by optical fiber 1877. Preferably, fiber 1877 terminates just within the distal end of hollow needle segment 1840. Proximal end portion 1841 of needle segment 1840 is secured to fiber 1877 by crimping. In this embodiment, the distal end of fiber 1877, encased in needle segment 1840, is manually advanced into the tissue by moving handle housing 1812 forward.

Referring to FIG. 32, handle housing 1912 is provided with tapered endpiece 1913 mounted thereto. Hollow needle 1940 extends through endpiece 1913 and into handle housing 1912. Optical fiber 1977 extends from the laser source, through hollow needle 1940 and terminates just proximate to the distal end of hollow needle 1940. Endpiece 1913 is secured to handle housing 1912 by an epoxy-type adhesive, by interference fit, or in any other convenient manner. In this embodiment, the distal end of hollow needle 1940 is manually advanced into the tissue by moving handle housing 1912 forward.

In Intra-Operative and Endoscopic TMR procedures, in order to make the diameter of the channel larger at the inside surface of the endocardium, (2 to 3 millimeters in diameter as is seen in alligator hearts), the speed at which the needle advances can be varied. If, for example, the heart wall is 15 millimeters thick, after the needle manually pierces the epicardium to a depth of 4 millimeters, it can be moved by the external actuator at a fast rate through the remainder of the epicardium, slower through the 4 to 5 millimeters inner portion of the endocardium and slowest through the last 5 to 6 millimeters of the endocardium.

Conversely, in a Percutaneous TMR procedure, the optical fiber is contained in a catheter inserted into an artery and extended through the aortic valve into the left ventricle. When the catheter is properly positioned against the chamber wall, which may be accomplished through imaging or electrical sending means, the channels are made partially through the heart wall by a SPECTRAPROBE needle that is attached to the optical fiber. The SPECTRAPROBE needle contains a central bore in which a lens, to diverge the laser beam, is mounted.

In this procedure, the needle emerges from the catheter and is positioned against the endocardium. The fiber and SPECTRAPROBE needle are advanced through the catheter the desired distance, while lasing, as described here before. The first 6 millimeters of lasing could be at a relatively slow rate and the next 4 to 5 millimeters of lasing would be at a faster rate, creating a larger diameter channel in the first 6 millimeters of the endocardium. In Percutaneous TMR, no extension of the SPECTRAPROBE device from the catheter is needed as the endocardium is less dense and more easily penetrated.

In all of the above disclosed embodiments, ultrasound may be used to assist the surgeon in determining the thickness of the heart wall. The ultrasound procedure, may be used before the TMR procedure with the physician remembering from the ultrasound image the thickness of the heart wall at various places, or during the TMR procedure, with the physician or an assistant periodically observing the ultrasound image display.

Conversely, an ultrasound emitting and receiving probe may be attached at the distal end of the needle collar or on a separate hand held device. The ultrasound image may be displayed on a TV monitor, so that the surgeon can visualize the thickness of the heart wall at the point where the optical fiber penetrates the heart wall. In addition, the penetration of the optical fiber into the heart chamber and steam bubbles, from the absorption of laser energy by blood in the chamber, can be visualized to confirm that the entire heart wall was penetrated.

In another preferred embodiment, the aforesaid ultrasound emitter/receiver may also transmit image data to a microcontroller, such as the one in the external actuator, wherein the microcontroller processes the data to determine the thickness of the heart wall. The microcontroller then operates the external actuator such that the needle is advanced to a distance that is equal to the thickness of the heart wall plus a few millimeters to insure complete penetration.

Furthermore, with regard to all of the embodiments depicted above, as the needle is advanced into the endocardium while the laser is firing, a plasma of hot gasses from the vaporization of tissue forms ahead of the needle and/or fiber. These hot gasses cannot escape backwards, as the tissue hugs the needle in the channel, and solid tissue remains ahead of fiber and/or needle. These hot gasses accumulate and cause the diameter of the channel to increase as the fiber and/or needle advance through the endocardium, which may result in a larger ultimate channel at the inner surface of the heart wall. However, a larger zone of coagulation about the channel and lateral damage to the myocardium may result. Consequently, it may be necessary to advance the needle and/or fiber at a given rate at a given energy level to achieve a desirable and uniform channel diameter and coagulation zone.

It will be readily apparent from the foregoing detailed description of the invention and from the illustrations thereof that numerous variations and modifications may be effected without departing from the true spirit and scope of the novel concepts or principles of this invention.

We claimed:

1. A surgical device for forming a channel within tissue with laser energy and comprising:

a housing;

an optical fiber for transmission of said laser energy secured to said housing and adapted for connection to a laser source;

a hollow needle defining an open bore surrounding at least a portion of said optical fiber; and a switch for activating said laser energy transmission, said switch being located within said housing, said location of said switch being adjustable.

2. The device of claim 1 further comprising a display for preselecting a distance that said optical fiber is to extend from said needle.

3. A surgical device for forming a channel within tissue with laser energy and comprising:

a housing;

an optical fiber for transmission of said laser energy secured to said housing and adapted for connection to a laser source;

a hollow needle defining an open bore surrounding at least a portion of said optical fiber;

a switch for activating said laser energy transmission; and an actuator rod including a radially extending ridge operably associated with said switch, said switch being a toggle switch having a movable projection and said ridge operates said switch by moving the projection while moving past said switch.

* * * * *